(12) United States Patent
Giordano

(10) Patent No.: US 7,470,670 B2
(45) Date of Patent: Dec. 30, 2008

(54) PEPTIDE INHIBITORS OF CYCLIN-DEPENDENT KINASE ACTIVITY AND USES THEREOF

(75) Inventor: Antonio Giordano, Radnor, PA (US)

(73) Assignee: Sbarro Health Research Organization, Inc., Radnor, PA (US)

( * ) Notice: Subject to any disclaimer, the term of this patent is extended or adjusted under 35 U.S.C. 154(b) by 0 days.

(21) Appl. No.: 11/582,871

(22) Filed: Oct. 17, 2006

(65) Prior Publication Data

US 2008/0124314 A1 May 29, 2008

(51) Int. Cl.
*A61K 38/00* (2006.01)
*C07K 1/00* (2006.01)

(52) U.S. Cl. ......................................... 514/12; 530/350
(58) Field of Classification Search .................. 530/350; 514/12
See application file for complete search history.

(56) References Cited

U.S. PATENT DOCUMENTS

| | | | |
|---|---|---|---|
| 5,340,739 | A | 8/1994 | Stevens et al. |
| 5,457,049 | A | 10/1995 | Giordano |
| 5,496,731 | A | 3/1996 | Xu et al. |
| 5,521,081 | A | 5/1996 | Inaoka et al. |
| 5,532,340 | A | 7/1996 | Giordano |
| 5,596,079 | A | 1/1997 | Smith et al. |
| 5,597,694 | A | 1/1997 | Munroe et al. |
| 5,654,170 | A | 8/1997 | Klinger et al. |
| 5,807,681 | A | 9/1998 | Giordano et al. |
| 5,840,506 | A | 11/1998 | Giordano |
| 6,297,357 | B1 | 10/2001 | Giordano |
| 6,663,856 | B1 | 12/2003 | Giordano |

FOREIGN PATENT DOCUMENTS

| | | |
|---|---|---|
| EP | 0 571 911 | 12/1993 |
| EP | 0 666 270 | 8/1995 |
| WO | WO 93/06244 | 4/1993 |
| WO | WO 94/11531 | 5/1994 |
| WO | WO 95/02328 | 1/1995 |
| WO | 99/08700 | * 2/1999 |

OTHER PUBLICATIONS

Zhu, "A Model for CDK2 in Maintaining Genomic Stability," Cell Cycle, vol. 3, No. 11, Nov. 2004, pp. 1358-1362.
Claudio, et al., Eighty-Sixth Annual Meeting American Association for Cancer Research, Mar. 18-22, 1995; vol. 36, p. 195, 1164.
Dai, et al., "Small Molecule Inhibotors Targeting Cyclin-Dependent Kinases as Anticancer Agents," Current Oncology Reports, vol. 6, 2004, pp. 123-130.
Deonarain, "Ligand-targeted Receptor-mediated Vectors for Gene Delivery," Expert Opinion on Therapeutic Patents, vol. 8, No. 1, 1998, pp. 53-69.
Eck, et al., "Gene-Based Therapy," Goodman & Gilman's The Pharmacological Basis of Therapeutics, Ninth Ed., 1996, Chapter 5, pp. 77-101.

Hogg, et al., "Detection of Heterozygous Mutations in the *RB1* Gene in Retinoblastoma Patients Using Single-strand Conformation Polymorphism Analysis and Polymerase Chain Reaction Sequencing," Oncogene, vol. 7, 1992, pp. 1445-1451.
Lifshitz, et al., "*bcr* Genes and Transcripts," Oncogene, vol. 2, 1998, pp. 113-117.
Olofsson, et al., "Abnormal Expression of Cell Cycle Regulators in *FUS-CHOP* Carrying Liposarcomas," International Journal of Oncology, vol. 25, 2004, pp. 1349-1355.
Sang, et al., "The Roles of Tumor Suppressors pRb and p53 in Cell Proliferation and Cancer," Molecular and Cellular Differentiation, vol. 3, No. 1, 1995, pp. 1-29.
Thomas, et al., "A Polymorphic Dinucleotide Repeat in Intron 1 of the Human Tissue Plasminogen Activator Gene," Human Molecular Genetics, vol. 1, No. 2, May 1992, 138.
Vieweg, et al., "Considerations for the Use of Cytokine-Secreting Tumor Cell Preparations for Cancer Treatment," Cancer Investigation, vol. 13, No. 2, 1995, 193-201.
Wilson, et al., "Gene Therapy of Cystic Fibrosis Lung Disease Using El Deleted Adenoviruses: A Phase I Trial," Human Gene Therapy, vol. 5, No. 4, Apr. 1994, pp. 501-519.
Woo, et al., "p130 and p107 Use a Conserved Domain to Inhibit Cellular Cyclin-Dependent Kinase Activity," Molecular and Cellular Biology, vol. 17, No. 7, Jul. 1997, pp. 3566-3579.
Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111, Nov. 1990, pp. 2129-2138.
Lazar, et al., "Transforming Growth Factor α: Mutation of Aspartic Acid 47 and Leucine 48 Results in Different Biological Activities," Molecular and Cellular Biology, vol. 8, No.3, Mar. 1988, pp. 1247-1252.
Tao, et al., "Studies of Aglycosylated Chimeric Mouse-Human IgG, Role of Carbohydrate in the Structure and Effector Functions Mediated by the Human IgG Constant Region," The Journal of Immunology, vol. 143, No. 8, Oct. 15, 1989, pp. 2595-2601.
Li, et al., "The Adenovirus E1A-associated 130-kD Protein is Encoded by a Member of the Retinoblastoma Gene Family and Physically Interacts with Cyclins A and E," Genes & Development, vol. 7, 1993, pp. 2366-2377.
Gu, et al., "Inhibition of CDK2 Activity In Vivo by an Associated 20K Regulatory Subunit," Nature, vol. 366, Dec. 16, 1993, pp. 707-710.
Claudio, et al., "p120/pR52 Has Growth Suppressive Properties Similar to yet Distinctive from Those of Retinoblastoma Family Members pRb and p107," Cancer Research, vol. 54, 1994, pp. 5556-5560.

(Continued)

Primary Examiner—Maryam Monshipouri
(74) Attorney, Agent, or Firm—Reed Smith, LLP; William J. McNichol, Jr.

(57) ABSTRACT

Novel polypeptides or derivatives comprising cdk2 binding site are disclosed. The novel polypeptides or derivatives have growth suppressive activity. Nucleic acids encoding those polypeptides are also disclosed. The polypeptides identified herein are also useful in methods for treating or preventing cancer. The treatment methods comprise administration of the polypeptide to the patient. The methods also comprise contacting the sample with the above-described polypeptide or derivative, wherein the polypeptide or derivative also comprises a covalently attached detectable moiety, then determining whether the polypeptide or derivative is binding cdk2 from the sample.

11 Claims, 6 Drawing Sheets

OTHER PUBLICATIONS

Baldi, et al., "Genomic Structure of the Human Retinoblastoma-related Rb2/p130 Gene," Proc. Natl. Acad. Sci. USA, vol. 93, 1996, pp. 4629-4632.

De Luca, et al., "A Unique Domain of pRb2/p130 Acts as an Inhibitor of Cdk2 Kinase Activity," J. Biol. Chem, vol. 272, 1997, pp. 20971-20974.

Baldi, et al., "The Rb2/p130 Gene Product is a Nuclear Protein Whose Phosphorylation is Cell Cycle Regulated," Journal of Cellular Biochemistry, vol. 59, 1995, pp. 402-408.

Pines, et al., "Isolation of a Human Cyclin cDNA: Evidence for Cyclin mRNA and Protein Regulation in the Cell Cycle and for Interaction with $p34^{cdc2}$," Cell, vol. 58, Sep. 8, 1989, pp. 833-846.

Gibbs, et al., "Pharmaceutical Research in Molecular Oncology," Cell, vol. 79, Oct. 21, 1994, pp. 193-198.

Koff, et al., "Formation and Activation of a Cyclin E-cdk2 Complex During the G1 Phase of the Human Cell Cycle," Science, New Series, vol. 257, No. 5077, Sep. 18, 1992, pp. 1689-1694.

Slightom, et al., "Nucleotide Sequence Analysis of 77.7 kb of the Human $V_\beta$T-Cell Receptor Gene Locus: Direct Primer-Walking Using Cosmid Template DNAs," Genomics, vol. 20, 1994, pp. 149-168.

Gura, "Systems for Identifying New Drugs Are Often Faulty," Science, vol. 278, No. 5340, Nov. 7, 1997, pp. 1041-1042.

Song, et al., "Specific Inhibition of Cyclin-Dependent Kinases and Cell Proliferation by Harmine," Biochemical and Biophysical Research Communications, vol. 317, 2004, pp. 128-132.

Senderowicz, "Small-molecule Cyclin-dependent Kinase Modulators," Oncogene, vol. 22, 2003, pp. 6609-6620.

Losiewicz, et al., "Potent Inhibition of CDC2 Kinase Activity by the Flavonoid L86-8275," vol. 201, No. 2, 1994, pp. 589-595.

Morgan, "Cyclin-Dependent Kinases: Engines, Clocks, and Microprocessors," Annu. Rev. Cell Dev. Biol., vol. 13, 1997, pp. 261-291.

Hsu, et al., "Proliferative Inhibition, Cell-cycle Dysregulation, and Induction of Apoptosis by Ursolic Acid in Human Non-Small Cell Lung Cancer A549 Cells," Life Sciences, vol. 75, 2004, pp. 2303-2316.

Hirata, et al., "Cloning and Expression of cDNA for a Human Thromboxane $A_2$ Receptor," Nature, vol. 349, Feb. 14, 1991, pp. 617-620.

Crystal, "Transfer of Genes to Humans: Early Lessons and Obstacles to Success," Science, New Series, vol. 270, No. 5235, Oct. 20, 1995, pp. 404-410.

Vorechovsky, et al., "Isolation of Cosmid and cDNA Clones in the Region Surrounding the *BTK* Gene at Xq21.3-q22," Genomics, vol. 21, 1994, pp. 517-524.

Harbour, et al., "Abnormalities in Structure and Expression of the Human Retinoblastoma Gene in SCLC," Science, New Series, vol. 241, No. 4863, Jul. 15, 1988, pp. 353-357.

Zheng, et al., "Development of 124 Sequence-Tagged Sites and Cytogenetic Localization of 217 Cosmids for Human Chromosome10," Genomics, vol. 22, 1994, pp. 55-67.

Sherr, "Cancer Cell Cycles," Science, New Series, vol. 274, No. 5293, Dec. 6, 1996, pp. 1672-1677.

Weinberg, "The Retinoblastoma Protein and Cell Cycle Control," Cell, vol. 81, May 5, 1995, pp. 323-330.

Andrews, et al., "Design, Synthesis, Biological Activity and Structural Analysis of Cyclic Peptide Inhibitors Targeting the Substrate Recruitment Site of Cyclin-Dependent Kinase Complexes," Org. Biomol. Chem., vol. 2, 2004, 2735-2741.

Gray, et al., "Exploiting Chemical Libraries, Structure, and Genomics in the Search for Kinase Inhibitors," Science, vol. 281, Jul. 24, 1998, pp. 533-538.

Matsumoto, et al., "A Centrosomal Localization Signal in Cyclin E Required for Cdk2-Independent S Phase Entry," Science, vol. 306, Oct. 29, 2004, pp. 885-888.

Al-Aynati, et al., "Overexpression of $G_1$-S Cyclins and Cyclin-Dependent Kinases During Multistage Human Pancreatic Duct Cell Carcinogenesis," Cllinical Cancer Research, vol. 10, Oct. 1, 2004, pp. 6598-6605.

Ohtsubo, et al., "Human Cyclin E, a Nuclear Protein Essential for the $G_1$-to-S Phase Transition," Molecular and Cellular Biology, vol. 15, No. 5, May 1995, pp. 2612-2624.

Stoppa-Lyonnet, et al., "Clusters of Intragenic *Alu* Repeats Predispose the Human C1 Inhibitor Locus to Deleterious Rearrangements," Proc. Natl. Acad. Sci. USA, vol. 87, Feb. 1990, pp. 1551-1555.

Whitehead, et al., "Identification of Novel Members of the Serum Amyloid a Protein Superfamily as Constitutive Apolipoproteins of High Density Lipoprotein," The Journal of Biological Chemistry, vol. 267, No. 6, Feb. 25, 1992, pp. 3862-3867.

Wilson, et al., "Human Hypoxanthine-Guanine Phosphoribosyltransferase," The Journal of Biological Chemistry, vol. 258, No. 10, May 25, 1983, pp. 6458-6460.

Hong, et al., "Structure of the Human Retinoblastoma Gene," Proc. Natl. Acad. Sci. USA, vol. 86, Jul. 1989, pp. 5502-5506.

Miller, et al., "Targeted Vectors for Gene Therapy," The FASEB Journal, vol. 9, Feb. 1995, pp. 190-199.

Giordano, et al., "Cell Cycle Regulation of Histone H1 Kinase Activity Associated with the Adenoviral Protein E1A," Science, vol. 253, Sep. 13, 1991, pp. 1271-1275.

Huang, et al., "Suppression of the Neoplastic Phenotype by Replacement of the RB Gene in Human Cancer Cells," Science, vol. 242, Dec. 16, 1988, pp. 1563-1566.

Paggi, et al., "Retinoblastoma Protein Family in Cell Cycle and Cancer: A Review," Journal of Cellular Biochemistry, vol. 62, 1996, pp. 418-430.

Kiess, et al., "Expression and Activity of the Retinoblastoma Protein (pRB)-Family Proteins, p107 and p130, during $L_6$ Myoblast Differentiation," Cell Growth & Diffentiation, vol. 6, Oct. 1995, pp. 1287-1298.

Lee, et al., "The Retinoblastoma Susceptibility Gene Encodes a Nuclear Phosphoprotein Associated With DNA Binding Activity," Nature, vol. 329, Oct. 1978, pp. 642-645.

Elledge, et al., "A New Human p34 Protein Kinase, CDK2, Identified by Complementation of a *cdc28* Mutation in *Saccharomyces cerevisiae*, is Homolog of *Xenopus* Egl," The EMBO Journal, vol. 10, 1991, pp. 2653-2659.

Ewen, et al., "Molecular Cloning, Chromosomal Mapping, and Expression of the cDNA for p107 a Retinoblastoma Gene Product-Related Protein," Cell, vol. 66, Sep. 20, 1991, pp. 1155-1164.

Antelman, et al., "Inhibition of Tumor Cell Proliferation In Vitro and In Vivo by Exogenous $p110^{RB}$, the Retinoblastoma Tumor Suppressor Protein," Oncogene, vol. 10, 1995, pp. 697-704.

Chellappan, et al., "The E2F Transcription Factor Is a Cellular Target for the RB Protein," Cell, vol. 65, Jun. 14, 1991, pp. 1053-1061.

Ewen, et al., "Interaction of p107 with Cyclin A Independent of Complex Formation with Viral Oncoproteins," Science, vol. 255, Jan. 3, 1992, pp. 85-87.

Xiong, "Why are there so many CDK inhibitors?," Biochimica et Biophysica Acta, vol. 1288, 1996, pp. 1-5.

Sherr, et al., "Inhibitors of Mammalian $G_1$ Cyclin-Dependent Kinases," Genes & Development, vol. 9, 1995, pp. 1149-1163.

Hu, et al., "The Regions of the Retinoblastoma Protein Needed for Binding to Adenovirus E1A or SV40 Large T Antigen are Common Sites for Mutations," The EMBO Journal, vol. 9, 1990, pp. 1147-1155.

Kamb, et al., "A Cell Cycle Regulator Potentially Involved in Genesis of Many Tumor Types," Science, vol. 264, Apr. 15, 1994, pp. 436-440.

Nobori, et al., "Deletions of the Cyclin-Dependent Kinase-4 Inhibitor Gene in Multiple Human Cancers," Nature, vol. 368, Apr. 21, 1994, pp. 753-756.

Morgan, et al., "Approaches to the Discovery of Non-Peptide Ligands for Peptide Receptors and Peptidases," Ann. Reports Med. Chem., 1989, vol. 24, pp. 243-252.

MacLachlan, et al., "Cyclins, Cyclin-Dependent Kinases and Cdk Inhibitors: Implications in Cell Cycle Control and Cancer," Critical Reviews in Eukaryotic Gene Expression, vol. 5, No. 2, 1995, pp. 127-156.

Zhu, et al., "Inhibition of Cell Proliferation by p107, a Relative of the Retinoblastoma Protein," Genes & Development, No. 7, 1993, pp. 1111-1125.

Orkin, et al., "Report and Recommendations of the Panel to Assess the NIH Investment in Research on Gene Therapy," Dec. 7, 1995.

Gahery-Segard, et al., "Phase I Trial of Recombinant Adenovirus Gene Transfer in Lung Cancer," J. Clin. Invest., vol. 100, No. 9, Nov. 1997, pp. 2218-2226.

Bellon, et al., "Aerosol Administration of a Recombinant Adenovirus Expression CFTR to Cystic Fibrosis Patients: A Phase I Clinical Trial," Human Gene Therapy, vol. 8, Jan. 1, 1997, pp. 15-25.

Roth, et al., "Gene Therapy for Non-Small Cell Lung Cancer: A Preliminary Report of a Phase I Trial of Adenoviral p53 Gene Replacement," Seminars in Oncology, vol. 25, No. 3, Suppl. 8, Jun. 1998, pp. 33-37.

Claudio, et al., "Intraarterial Chemotherapy Through Carotid Transposition in Advanced Head and neck Cancer," Cancer, vol. 65, No. 7, Apr. 1, 1990, pp. 1465-1471.

Rilke, et al., "Prognostic Significance of Her-2/NEU Expression in Breast Cancer and its Relationship to Other Prognostic Factors," Int. J. Cancer, vol. 49, 1991, pp. 44-49.

DeCaprio, et al., "The Product of the Retinoblastoma Susceptibility Gene Has Properties of a Cell Cycle Regulatory Element," Cell, vol. 58, Sep. 22, 1989, pp. 1085-1095.

Bargmann, et al., The neu Oncogene Encodes an Epidermal Growth Factor Receptor-Related Protein, Nature, vol. 319, Jan. 16, 1986, pp. 226-230.

Coussens, et al., "Tyrosine Kinase Receptor with Extensive Homology to EGF Receptor Shares Chromosomal Location with neu Oncogene," Science, vol. 230, Dec. 6, 1985, pp. 1132-1139.

Slamon, et al., "Studies of the HER-2/neu Proto-oncogene in Human Breast and Ovarian Cancer," Science, vol. 244, May 12, 1989, pp. 707-712.

Ross, et al., "Gene Therapy in the United States: A Five-Year Status Report," Human Gene Therapy, vol. 7, Sep. 10, 1996, pp. 1781-1790.

Feldman, et al., "Prevention of Restenosis After Coronary Angioplasty: Towards a Molecular Approach?," Fundamental & Clinical Pharmacology, vol. 9, 1995, pp. 8-16.

Claudio, et al., "Mutations in the Retinoblastoma-related Gene RB2/p130 Lung Tumors and Suppression of Tumor Growth in Vivo by Retrovirus-mediated Gene Transfer," Cancer Research, vol. 60, 2001, pp. 372-382.

Raj, et al., "Characterization of Giliorna Cells Derived From Human Polyomavirus-induced Brain Tumors in Hamsters," International Journal of Oncology, vol. 7, 1995, pp. 801-808.

Alley, et al., "Feasibility of Drug Screening with Panels of Human Tumor Cell Lines Using a Microculture Tetrazolium Assay," Cancer Research, vol. 48, 1988, pp. 589-601.

Baldi, et al., "Differential Expression of the Retinoblastoma Gene Family Members pRb/p105, p107, and pRb2/p130 in Lung Cancer," Clinical Cancer Research, vol. 2, Jul. 1996, pp. 1239-1245.

Barnes, et al., "Gene Therapy and Ovarian Cancer: A Review," Obstetrics & Gynecology, vol. 89, No. 1, Jan. 1997, pp. 145-155.

Claudio, et al., "Factors Affecting Response and Survival in Advanced Head and Neck Cancers Treated With Intraarterial Chemotherapy," Regional Cancer Treatment, vol. 4, 1992, pp. 180-187.

Gossen, et al., "Tight Control of Gene Expression in Mammalian Cells by Tetracycline-responsive Promoters," Proc. Natl. Acad. Sci. USA, vol. 89, Jun. 1992, pp. 5547-5551.

Gunning, et al., "Isolation and Characterization of Full-Length cDNA Clones for Human α-, β-, and γ-Actin mRNAs: Skeletal but Not Cytoplasmic Actins Have an Amino-Terminal Cycteine that Is Subsequently Removed," Molecular and Cellular Biology, vol. 3, No. 5, May 1983, pp. 787-795.

Guy, et al., "Expression of the neu Protooncogene in the Mammary Epithelium of Transgenic Mice Induces Metastatic Disease," Proc. Natl. Acad. Sci. USA, vol. 89, Nov. 1992, pp. 10578-10582.

Hanania, et al., "Recent Advances in the Application of Gene Therapy to Human Disease," The American Journal of Medicine, vol. 99, Nov. 1995, pp. 537-552.

Kern, et al., "C-erbB-2 Expression and Codon 12 K-ras Mutations Both Predict Shortened Survival for Patients with Pulmonary Adenocarcinomas," J. Clin. Invest., vol. 93, Feb. 1994, pp. 516-520.

Neri, et al., "Nuclear Scaffold Proteins Are Differently Sensitive to Stabilizing Treatment by Heat or $Cu^{++}$," The Journal of Histochemistry & Cytochemistry, vol. 45, No. 2, 1997, pp. 295-305.

Park, et al., "Amplification, Overexpression, and Rearrangement of the erbB-2 Protooncogene, in Primary Human Stomach Carcinomas," Cancer Research, vol. 49, Dec. 1, 1989, pp. 6605-6609.

Pupa, et al., "Macrophage Infiltrate and Prognosis in c-erbB-2-Overexpressing Breast Carcinomas," Journal of Clinical Oncology, vol. 14, No. 1, Jan. 1996, pp. 85-94.

Roth, et al., "Gene Therapy for Cancer: What Have We Done and Where Are We Going?," Journal of the National Cancer Institute, vol. 89, No. 1, Jan. 1, 1997, pp. 21-39.

Davis, et al., "Current Progress in the Gene Therapy of Cancer," Current Opinion in Oncology, vol. 8, 1996, pp. 499-508.

Sang, et al., "Generation of Site-Directed Mutagenesis by Extralong, High-Fidelity Polymerase Chain Reaction," Analytical Biochemistry, vol. 233, 1996, pp. 142-144.

Shockett, et al., "A Modified Tetracyline-regulated System Provides Autoregulatory, Inducible Gene Expression in Cultured Cells and Transgenic Mice," Proc Natl. Acad. Sci. USA, vol. 92, Jul. 1995, pp. 6522-6526.

Tagliabue, et al., "Selection of Monoclonal Antibodies Which Include Internalization and Phosphorylation of $p185^{HER2}$ and Growth Inhibition of Cells With HER2/NEU Gene Amplification," Int. J. Cancer, vol. 47, 1991, pp. 933-937.

Wessel, et al., "Method for the Quantitative Recovery of Protein in Dilute Solution in the Presence of Detergents and Lipids," Anal. Biochemistry, vol. 138, 1984, pp. 141-143.

Susini, et al., "Expression of the Retinoblastoma-Related Gene Rb2/p130 Correlates With Clinical Outcome in Endometrial Cancer," Journal of Clinical Oncology, vol. 16, No. 3, Mar. 1998, pp. 1085-1093.

Eck, et al., "Treatment of Advanced CNS Malignancies With the Recombinant Adenovirus H5.010RSVTK: A Phase I Trial," Human Gene Therapy, vol. 7, Aug. 1, 1996, pp. 1465-1482.

Huttner, et al., "NA-mediated Gene Transfer Without Carrier DNA," The Journal of Cell Biology, vol. 91, Oct. 1981, pp. 153-156.

Zacksenhaus, et al., "A Bipartite Nuclear Localization Signal in the Retinoblastoma Gene Product and Its Importance for Biological Activity," Molecular and Cellular Biology, vol. 13, No. 8, Aug. 1993, pp. 4588-4599.

Hannon, et al., "Isolation of the Rb-related p130 Through Its Interaction With CDK2 and Cyclins," Genes & Development, vol. 7, 1993, pp. 2378-2391.

Tursz, et al., "Phase I Study of a Recombinant Adenovirus-Mediated Gene Transfer in Lung Cancer Patients," Journal of the National Cancer Institute, vol. 88, No. 24, Dec. 18, 1996, pp. 1857-1863.

Sterman, et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," Human Gene Therapy, vol. 9, May 1, 1998, pp. 1083-1092.

Verma, et al., "Gene Therapy—Promises, Problems and Prospects," Nature, vol. 389, Sep. 18, 1997, pp. 239-242.

Sinnett, et al., "Alu RNA Transcripts in Human Embryonal Carcinoma Cells. Model of Post-transcriptional Selection of Master Sequences," Journal of Molecular Biology, vol. 226, 1992, pp. 689-706.

Bagella, et al., "A small molecule based on the pRb2/p130 spacer domain leads to inhibition of cdk2 activity, cell cycle arrest and tumor growth reduction in vivo," Oncogene, 2007, vol. 26, pp. 1829-1839.

* cited by examiner

A

B

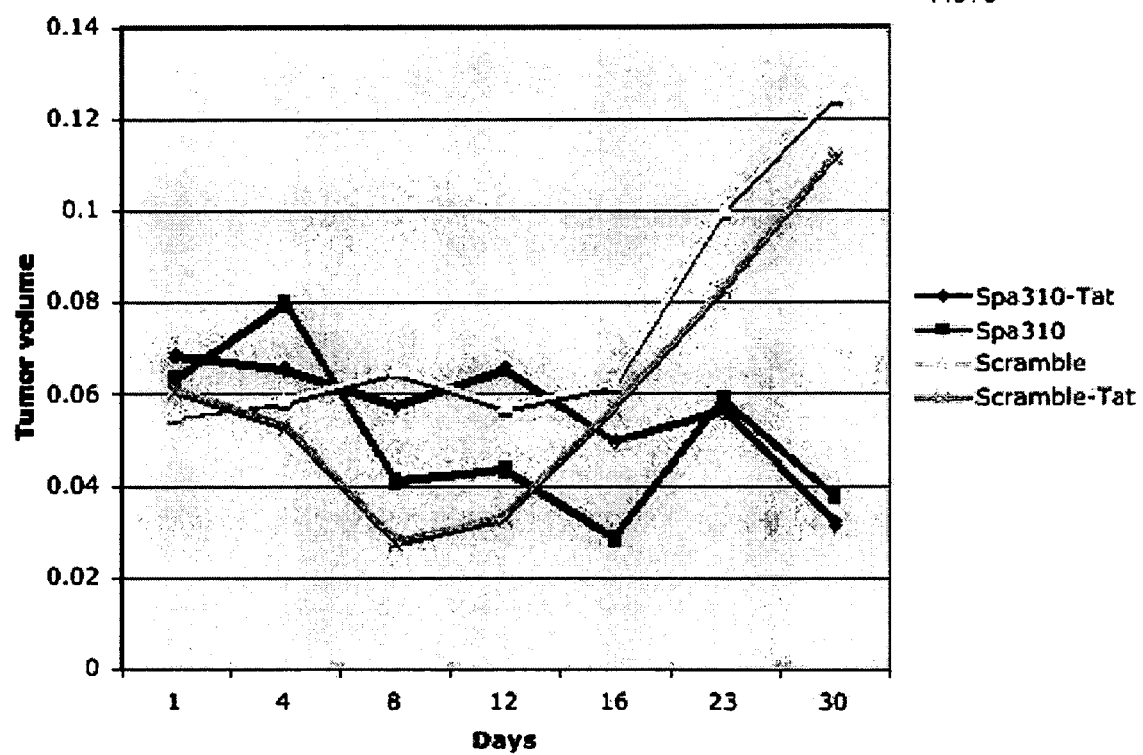

PEPTIDE INHIBITORS OF CYCLIN-DEPENDENT KINASE ACTIVITY AND USES THEREOF

The subject matter of this application was made possible, in part, with funding from the U.S. Government. The Government may have certain rights.

TECHNICAL FIELD OF THE INVENTION

Generally, the present invention relates to inhibitors of cyclin-dependent kinase activity and, more particularly, pharmaceutical compositions containing the compounds, and the use of the compounds for the treatment of cancer and tumors. The present invention especially provides isolated and specific active components of the pRb2/p130 gene responsible for growth suppressive activity.

BACKGROUND OF THE INVENTION

One of the main goals in the development of novel therapeutics for proliferative disorders is to generate selective small molecules that potently inhibit cell cycle progression. Several studies have provided evidence of the critical involvement of cyclin/cdk complexes at specific cell cycle regulatory checkpoints (Morgan, 1997, Annu Rev Cell Dev Biol, 13, 261-91; Sherr, 1996, Science, 274, 1672-7). Progression through the cell cycle is driven by activation and deactivation of cyclin/cdk complexes, which start a fundamental cascade of events leading to DNA replication and chromosomal segregation. Tumor development is closely associated with alteration and deregulation of cdks and their regulators, suggesting that inhibitors (antagonists) of cdks may be useful anticancer therapeutics. Therefore, targeting cdk activity has become an attractive strategy in cancer therapy, since it could potentially create a rationally designed inhibitor of a specific process that leads a cell to malignant transformation. To date, several families of chemical inhibitors targeted against different cdk activities have been described (Gray et al., 1998, Science, 281, 533-8; Losiewicz et al., 1994, Biochem Biophys Res Commun, 201, 589-95) and, for some of them, their anticancer therapeutic potential has been demonstrated in preclinical studies (Dai & Grant, 2004, Curr Oncol Rep, 6, 123-30). Recent attention has been focused on biological molecules, especially peptide antagonists, rather than chemotherapeutic agents, that combine the effectiveness of arresting cellular growth through interaction with important cell cycle checkpoint regulators and the low risk of unexpected adverse reactions, thus improving clinical safety and patient tolerability. Therefore, development of pharmacological small peptide molecules able to inhibit cdk activity could be an alternative mechanism-based therapy of great interest in the treatment of neoplasms or other proliferative disorders.

Cdk2 is known to be active in complex with cyclin E at the G1-S boundary, and in complex with cyclin A during S phase progression (Sherr, 1996, Science, 274, 1672-7). Cyclin-dependent kinase 2 (cdk2) is considered the prototypic cell cycle kinase and plays a crucial role in the regulation of cell cycle progression in mammalian cells (Koff et al., 1992, Science, 257, 1689-94; Ohtsubo et al., 1995, Mol Cell Biol, 15, 2612-24). Cdk2 is necessary to pass the G1 restriction point and to drive cells into DNA replication. This enzyme determines whether a cell will leave its resting phase and enter the S phase, a critical determining point, after which a cell is committed to divide.

Among the target substrates that cdks phosphorylate are the members of the retinoblastoma (Rb) family proteins, which play a pivotal role as negative regulators of cell cycle progression (Claudio et al., 1994, Cancer Res, 54, 5556-60). This family includes the product of the retinoblastoma susceptibility gene, the pRb/p105 protein, and the related p107 and pRb2/p130 proteins (Hannon et al., 1993, Genes Dev, 7, 2378-91; Mayol et al., 1993, Oncogene, 8, 2561-6; Paggi et al., 1996, J Cell Biochem, 62, 418-30). They share the ability to recruit chromatin-remodeling enzymes and their best characterized targets are the members of the E2F/DP family of transcription factors, generally referred to as E2F (Weinberg, 1995, Cell, 81, 323-30). Both pRb2/p130 and p107 are able to bind cdk2/cyclins A and E (Claudio et al., 1996, Cancer Res, 56, 2003-8). Overexpression of cdk2 with associated cyclins has been shown in several tumors (Al-Aynati et al., 2004, Clin Cancer Res, 10, 6598-605; Olofsson et al., 2004, Int J. Oncol, 25, 1349-55; Zhu, 2004, Cell Cycle, 3). Furthermore, cdk2 has been recently found to be required for centrosome duplication in mammalian cells (Matsumoto et al., 1999, Curr Biol, 9, 429-32; Matsumoto & Maller, 2004, Science, 306, 885-8) suggesting that inhibition of cdk2 activity would be an effective anti-cancer approach. In addition, cdk2 has rapidly emerged as a potential inhibition target by small molecule drugs, which should eventually lead to the development of effective therapies for proliferative disorders (Andrews et al., 2004, Org Biomol Chem, 2, 2735-41; Dai & Grant, 2004, Curr Oncol Rep, 6, 123-30; Gibbs & Oliff, 1994, Cell, 79, 193-8; Hsu et al., 2004, Life Sci, 75, 2303-16; Senderowicz, 2003, Oncogene, 22, 6609-20; Song et al., 2004, Biochem Biophys Res Commun, 317, 128-32).

Previously, it was demonstrated that pRb2/p130, a member of the retinoblastoma family of proteins, acts during cell growth suppression as an inhibitor of cdk2 activity (De Luca et al., 1997, J Biol Chem, 272, 20971-4). The spacer region of pRb2/p130 has a unique amino acid sequence among the other members of the retinoblastoma family, and it is responsible for this inhibitory effect on cdk2 (U.S. Pat. No. 6,297, 357). U.S. Pat. Nos. 5,457,049; 5,532,340; 5,807,681; 5,840, 506; and 6,663,856, each of which is herein incorporated by reference in its entirety including any references cited therein, also disclose the nucleic acid and polypeptide sequences of the pRB2/p130 spacer domain. The identification and isolation of further true cdk inhibitor peptides exhibiting growth suppressive activity would be useful for designing treatments for cancer therapy; either as an alternative to or in conjunction with other known therapies.

SUMMARY OF THE INVENTION

The invention relates to the discovery of pharmacological polypeptide molecules that are able to inhibit cell cycle progression and induce growth arrest when expressed in cells and promote tumor regression in vivo. The polypeptide molecules disclosed in the present invention contain a fragment of the full-length sequence of pRb2/p130 spacer domain (amino acids 616-828) (SEQ ID NO. 20). The peptide molecules are specific to and capable of inhibiting cdk2-dependent histone phosphorylation and halting cellular growth by arresting cells in the $G_0/G_1$ phase of the cell cycle.

Accordingly, in one aspect, the invention provides cdk2 kinase activity inhibiting peptides and nucleic acid fragments of pRb2/p130 encoding the polypeptides, referred to herein as Spa peptide molecules (Spa polypeptides/Spa peptides) and Spa nucleic acid molecules (Spa nucleic acid), respectively.

The Spa peptide molecules contain contiguous amino acids of between about 34 to about 144 amino acids long and contain at least amino acids 641 to 674 of the spacer domain wherein the Spa peptide molecules are capable of inhibiting cdk2 kinase activity; and are about 39 to 70 amino acids in length, beginning with amino acid 641 and including amino acid 674 of the spacer domain.

The invention provides at least 10 different Spa peptide molecules as well as functionally equivalent subsets of these molecules, including but not limited to deletion mutants and variants thereof. For purposes of the present invention, variants are only those that carry amino acid substitutions in the fragments from the spacer molecule. The deletion mutants and variants are collectively referred to herein as "mutants," include only those determined to have cdk2 inhibitory activity.

According to an embodiment, the invention provides a cdk2 activity inhibiting polypeptide having one of the following amino acid sequences based upon the native amino acid sequence of pRb2/p130 (SEQ ID NO:21: amino acids 641 to 702 (62 amino acids long) designated Spa38 (SEQ ID NO: 1); amino acids 641 to 682 (42 amino acids long) designated Spa311 (SEQ ID NO:2); amino acids 641-679 (39 amino acids long) designated Spa310 (SEQ ID NO:3); amino acids 559 to 682 (124 amino acids long) designated Spa 319 (SEQ ID NO:4); amino acids 641-771 (131 amino acids long) designated Spa313 (SEQ ID NO:5); amino acids 616-682 (67 amino acids long) designated Spa314 (SEQ ID NO:6); amino acids 559-702 (144 amino acids long) designated Spa315 (SEQ ID NO:7); amino acids 616 to 702 (87 amino acids long) designated Spa316 (SEQ ID NO:8); amino acids 559-679 (121 amino acids long) designated Spa317 (SEQ ID NO:9); amino acids 616 to 679 (64 amino acids long) designated Spa318 (SEQ ID NO: 10); amino acids 641 to 674 (34 amino acids long) designated Spa20 (SEQ ID NO:11); amino acids 641 to 675 (35 amino acids long) designated Spa21 (SEQ ID NO:12); amino acids 641 to 676 (36 amino acids long) designated Spa22 (SEQ ID NO:13); amino acids 641 to 677 (37 amino acids long) designated Spa23 (SEQ ID NO: 14); and amino acids 641 to 678 (38 amino acids long) designated Spa24 (SEQ ID NO:15) or the fragments/deletion mutants of any of SEQ ID NOs: 1-15.

The variants can be different from the fragments of the spacer molecules described herein (e.g., Spa310 peptide, Spa311 peptide or Spa38 peptide) at one, two, three, four, or five amino acid positions. In the most common instances, such differences will involve conservative amino acid substitutions. In one embodiment, the amino acid sequence of a variant of the present invention is identical to that set forth in SEQ ID NOs: 1, 2 or 3 except that, over the entire length corresponding to the amino acid sequence of SEQ ID NOs: 1, 2 or 3, the variant amino acid sequence has one, two, three, four, or five amino acid substitutions, preferably, conservative amino acid substitutions.

Accordingly, for the purposes of the present invention, by "peptide" it is meant to include peptides having any of SEQ ID NOs: 1-15 or fragments or mutants thereof having cdk2 inhibitory activity. These peptide sequences, which retain the inhibitory activity, can be prepared synthetically in accordance with well-known methods such as solid or solution phase peptide synthesis. Alternatively, peptides of the present invention may be synthesized recombinantly.

These and other aspects of the invention will be described in greater detail herein.

BRIEF DESCRIPTION OF THE DRAWINGS

The present invention is best understood with reference to the following detailed description of the invention and the drawings in which:

FIG. 6 is a graph of an embodiment of the invention showing tumor suppressive effects of four different peptides (TAT-Spa310, TAT-SCRAMBLE, Spa310 and SCRAMBLE) in tumor bearing mice.

DETAILED DESCRIPTION

Figure 1:
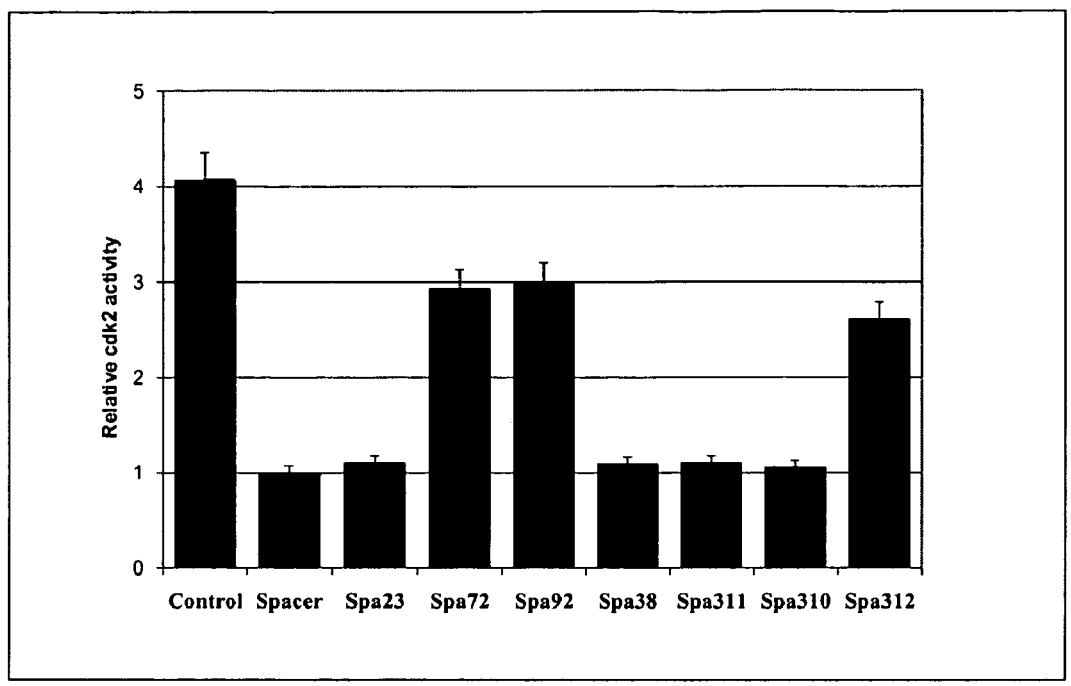
FIG. 1 shows an embodiment of the invention where cdk2 was immunoprecipitated with anti-cdk2 polyclonal antibody from exponentially growing NIH/3T3, incubated with equal amounts of GST-fusion proteins in a kinase reaction mixture, and assessed for phosphorylation ability of the histone H1 substrate; and using SDS-PAGE gels (10%), various constructs of pRb2/p130 maintain the inhibitory effects of the pRB2/p130 spacer domain on cdk2 kinase activity.

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

The invention relates in part to the identification and use of peptides that specifically inhibit cdk2 activity. These peptides are referred to herein as Spa peptide molecules. These peptide molecules are able to greatly inhibit cdk2-dependent histone phosphorylation and halt cellular growth by arresting cells in the G0/G1 phase of the cell cycle. The peptides and their functional equivalents are useful in the diagnosis and treatment of disorders characterized by cdk2 expression or overexpression. In particular, the peptides and their functional equivalents are useful in the treatment of neoplasms or other proliferative disorders including cancer and tumors, in particular for the prevention and inhibition of tumor colonization. They are also useful in the isolation and, optionally, removal of cells that overexpress cdk2 (e.g., tumor cells). These peptides can also be used to identify further Spa peptide molecules.

According to an embodiment, the invention involves, in various related and interconnected aspects, isolated cdk2-inhibiting peptides, functional equivalents and modifications and variants thereof, unique fragments thereof, nucleic acid molecules encoding the foregoing, as well as diagnostics and therapeutics relating thereto.

According to an embodiment, the invention includes a composition having a cdk2 activity inhibiting polypeptide having one of the following amino acid sequences based upon the native amino acid sequence of pRb2/p130 (SEQ ID NO:21): amino acids 641 to 702 (62 amino acids long) designated Spa38 (SEQ ID NO:1); amino acids 641 to 682 (42 amino acids long) designated Spa311 (SEQ ID NO:2); amino acids 641-679 (39 amino acids long) designated Spa310 (SEQ ID NO:3); amino acids 559 to 682 (124 amino acids long) designated Spa319 (SEQ ID NO:4); amino acids 641-771 (131 amino acids long) designated Spa313 (SEQ ID NO:5); amino acids 616-682 (67 amino acids long) designated Spa314 (SEQ ID NO:6); amino acids 559-702 (144 amino acids long) designated Spa315 (SEQ ID NO:7); amino acids 616 to 702 (87 amino acids long) designated Spa 316 (SEQ ID NO:8); amino acids 559-679 (121 amino acids long) designated Spa317 (SEQ ID NO:9); amino acids 616 to 679 (64 amino acids long) designated Spa318 (SEQ ID NO: 10); amino acids 641 to 674 (34 amino acids long) designated Spa20 (SEQ ID NO:11); amino acids 641 to 675 (35 amino acids long) designated Spa21 (SEQ ID NO:12); amino acids 641 to 676 (36 amino acids long) designated Spa22 (SEQ ID NO:13); amino acids 641 to 677 (37 amino acids long) designated Spa23 (SEQ ID NO:14); and amino acids 641 to 678 (38 amino acids long) designated Spa24 (SEQ ID NO: 15) or the fragments/deletion mutants of any of SEQ ID NOs: 1-15.

The variants can be different from the fragments of the spacer molecules described herein (e.g., Spa310 peptide, Spa311 peptide or Spa38 peptide) at one, two, three, four, or five amino acid positions. In the most common instances, such differences will involve conservative amino acid substitutions. In one embodiment, the amino acid sequence of a variant of the present invention is identical to that set forth in SEQ ID NOs: 1, 2 or 3 except that, over the entire length corresponding to the amino acid sequence of SEQ ID NOs: 1, 2 or 3, the variant amino acid sequence has one, two, three, four, or five amino acid substitutions, preferably, conservative amino acid substitutions. In some embodiments, variants are peptides that have at least 80%, at least 85%, at least 90%, or at least 95% identity (match) but not 100% identity over the full length of the Spa peptides described herein and determined to have cdk2 inhibitory activity. Conservative substitutions of amino acids include, but are not limited to substitutions made amongst amino acids within the following groups: (i) F, Y, W; (ii) K, R, H; (iii) M, I, L, V; and (iv) E, D.

According to a preferred embodiment, the Spa peptide molecules of the present invention are no more than 70 amino acids long polypeptides, contain at least amino acids 641-674, and are of sufficient length capable of inhibiting cdk2 kinase activity. A functionally equivalent variant of such a 70 amino acid long polypeptide is one that is identical to the 70 amino acid long polypeptide except that, over the entire length corresponding to the amino acid sequence of the 70 amino acid polypeptide, the variant has one, two, three, four, or five conservative amino acid substitutions.

According to an embodiment, the invention also provides deletion mutants of SEQ ID NO: 1-SEQ ID NO: 15. In one embodiment, mutants of the present invention that are capable of exhibiting cdk2 inhibitory activity can be defined by generating deletion mutants beginning at the amino-terminus and/or COOH terminus of the full-length sequence of pRb2/p130 spacer domain. In addition, chimeric fusion proteins corresponding to these mutant sequences are also part of the invention.

For achieving cdk2 inhibitory activity and the associated growth suppressive effects, the Spa peptide molecules can be used as such or fused to a second polypeptide or conjugated to an agent. According to a preferred embodiment of the present invention, a given Spa peptide molecule is fused to a second polypeptide (e.g., the HIV Tat-derived peptide with the sequence GRKKRRQRRR (SEQ ID NO:16), glutathione S-transferase, His-tag) via, for example, a disulfide bond, a thio-ether linkage or a peptide bond. In another embodiment, the peptide is conjugated to an agent. The agent may include, but is not limited to a toxin, a radioactive molecule, a detectable label, an imaging agent, a diagnostic agent, a chemotherapeutic agent, an immunomodulatory agent, and/or a translocating agent. The translocating agent can be used to translocate the peptide or preferably a therapeutic agent attached to the peptide into the cell in order to deliver the therapeutic agent to the cell. According to another embodiment, the peptide may be used together with an agent that functions in the cytoplasmic compartment of a cell, such as for example an agent that inhibits the cytoskeleton, or inhibits spindle formation. Several of these latter types of agents are known to be chemotherapeutic agents. In yet another embodiment, the peptide may be conjugated to another peptide such as one with binding specificity for cdk2. In another embodiment, the composition includes the peptide with a liposome or viral particle (e.g., for delivery in gene therapy).

The functional equivalents of Spa peptides can include peptidomimetics. In one embodiment, the functional equivalent may be chosen from a phage library member, a synthetic peptide library member, a combinatorial chemical library member, and a peptide mimetic.

According to an embodiment, the composition may further contain a pharmaceutically acceptable carrier, and optionally, the peptide or functional equivalent thereof is present in an effective amount. In other embodiments, the composition further contains another therapeutic agent including but not limited to an anti-cancer agent. The composition may be provided in a delivery vehicle well-known in the art, preferably in a sustained release form. In another aspect, a pharmaceutical preparation is provided having one or a combination of the afore-mentioned compositions and a pharmaceutically acceptable carrier. The pharmaceutical preparation and compositions may be in a sustained release vehicle.

According to an embodiment, the invention also provides for isolated nucleic acid molecules that code for Spa peptides and a composition containing the same. Thus, in yet another aspect, an isolated nucleic acid molecule is provided having (a) a nucleic acid molecule which codes for a peptide having an amino acid sequence of SEQ ID NOs: 1-15, preferably, SEQ ID NO: 1, SEQ ID NO: 2, or SEQ ID NO: 3 or functionally equivalent fragments thereof, (b) degenerates of (a); and (c) full-length complements of (a) and (b). Using the amino acid sequence of SEQ ID NO: 1, SEQ ID NO: 2, or SEQ ID NO: 3 provided herein, one of ordinary skill in the art can readily determine the nucleic acid sequences that are degenerates thereof.

According to an embodiment, the invention further provides an expression vector comprising the afore-mentioned isolated nucleic acid molecule, preferably operably linked to a promoter, and host cells and/or proliferating cells transformed or transfected with the expression vectors.

In another aspect, the invention provides a method for preventing or treating a disorder (e.g., neoplasms or tumor cell proliferation) characterized by cdk2 overexpression. The method can be used to prevent the disorder in a subject at risk of developing the disorder or, alternatively, to treat the disorder in a subject having the disorder. In embodiments of either, the methods further comprise first selecting a subject to be treated (e.g., a subject having the disorder or a subject at risk of developing the disorder). The method involves administering to a subject in need of such treatment a Spa peptide that inhibits cdk2 activity. In certain preferred embodiments, the Spa peptide may have an amino acid sequence of SEQ ID NO: 1, SEQ ID NO:2, and/or SEQ ID NO:3, or functional equivalents thereof.

According to an embodiment, the Spa peptide or functional equivalent thereof may be administered in an amount effective to inhibit the disorder. In other embodiments, the method may involve co-administering an anti-cancer agent to the subject. In these latter embodiments, the peptide and the anti-cancer agent are co-administered in a combined effective amount to inhibit the disorder. In related aspects of the foregoing methods non-peptide small molecules that functionally and/or structurally mimic the Spa peptides of the invention can also be used in place of the Spa peptides.

In one embodiment, the disorder is in or is likely to be in a tissue such as, but not limited to the lung, brain, breast, ovary, uterus, cervix, gastrointestinal tissue, colon, stomach, and bladder. In important embodiments, the disorder is a cancer. The cancer may be a primary tumor or a metastasis. The cancer may include but is not limited to lung cancer including non-small lung cancer, breast cancer, ovarian cancer (including endometrioid carcinoma), osteosarcoma, cervical cancer, colorectal cancer (e.g., colorectal adenomas and adenocarcinomas), thyroid cancer, prostate cancer, stomach cancer, and bladder cancer.

According to an embodiment, the peptide may be administered systemically. In another embodiment, the peptide may be administered locally. In yet another embodiment, the peptide may be administered in a plurality of administrations. In another embodiment, the method further involves administering to the subject an anti-cancer agent. The invention further provides a method for inhibiting/preventing tumor cell metastasis by administering to a subject in need of such treatment one or a combination of any of the afore-mentioned peptides or functional equivalents in an amount effective to prevent the formation or development of a metastasis. The metastasis may be present in, but is not limited to bone marrow, lung, brain, and/or liver.

According to an embodiment, the invention provides a method for detecting cells characterized by cdk2 overexpression involving delivering a Spa peptide, that in some embodiments has an amino acid sequence selected from the group consisting of SEQ ID NO: 1, SEQ ID NO:2, and SEQ ID NO:3 or functional equivalent thereof, to cells, and evaluating cell cycle distribution to determine the distribution of cells through the G1, S and or G2/M phases of the cell cycle, wherein cells exposed to the Spa peptide being present in G1 phase of the cell cycle in greater percentage than control cells (i.e., cells not exposed to the Spa peptide) is indicative of cdk2 overexpression by the cells.

In one embodiment, the delivering occurs in vivo and the peptide is administered to a subject either systemically or locally. In some embodiments, the peptide is conjugated to a detectable label. The detectable label may include, but is not limited to a radioisotope, a contrast agent, and/or a gaseous agent.

In one embodiment, the cells are breast tissue cells. In another embodiment, the cells are present in a population selected from the group consisting of bone marrow tissue, lung tissue, brain tissue, and liver tissue. In a related embodiment, the cells are harvested from a subject having a disorder characterized by cdk2 over-expression, prior to treating the subject with gene therapy or radiation or chemotherapy. The disorder characterized by cdk2 over-expression may be non-small cell lung cancer, but is not so limited.

According to an embodiment, the present invention includes a method for identifying a compound that interferes with or inhibits interaction between cdk2 and a Spa peptide (that preferably comprises an amino acid having a sequence of SEQ ID NO: 1, SEQ ID NO:2, or SEQ ID NO:3, or functional equivalent thereof). The method may involve the following steps: performing a first assay between cdk2 and the peptide or functional equivalent thereof to obtain a first assay result; performing a second assay between cdk2 and the peptide or functional equivalent thereof in the presence of a compound to obtain a second assay result; and comparing the first and second assay results to determine whether the compound inhibits interaction between cdk2 and the peptide or functional equivalent thereof. The method may also include a negative pre-screen in which compounds are initially tested and negatively selected based on their ability to bind to cyclins and/or cdks. In one embodiment, the compound is a molecular library member. The molecular library may include, but is not limited to a peptide library such as a phage display peptide library, a peptidomimetic library, a combinatorial chemistry library, a synthetic peptide library, and a natural compound library.

EXAMPLES

The following working examples are provided to demonstrate preferred embodiments of the invention, but of course, should not be construed as in any way limiting the scope of the present invention. The examples below were carried out using conventional techniques that are well-known and routine to those of skill in the art, except where otherwise described in detail. Further, it should be appreciated by those of skill in the art that the techniques disclosed in the examples represent techniques found by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Deletion Mutants of pRb2/p130 Spacer Region and Their cdk2 Inhibitory Activity

Different portions of the pRb2/p130 spacer region were prepared, expressed as GST-fusion proteins and assayed for their kinase inhibitory activity as follows:

Cell culture and transfections: The NIH/3T3 cell line was obtained from the American Type Culture Collection (ATCC, Rockville, Md.) and was grown at 37° C., in a 5% CO2/95% atmosphere, in Dulbecco's modified Eagle's medium (Mediatech Inc., Herndon, Va.) supplemented with fetal bovine serum (FBS) (Mediatech Inc., Herndon, Va.). Transfections were performed using the Fugene transfectant reagent (Roche Applied Science, Indianapolis, Ind.) according to the manufacturer's protocol.

Constructs preparation: A prokaryotic expression vector pGEX-2T (Stratagene Inc., La Jolla Calif.) and polymerase chain reaction (PCR) were used to generate chimeric Glutathione-S-Transferase constructs. The primers used by PCR to amplify the fragments that were subcloned in the pGEX-2T were derived from the 5' and 3' ends of different regions of the spacer domain of pRb2/p130. The nucleotide and amino acid positions, and the fragment length in base pairs and amino acids are shown in Table 1. The mammalian expression vector pEF6/V5-His TOPO (Invitrogen Corp, Carlsbad, Calif.) was used to generate the constructs pEF6/V5-His-spacer and pEF6/V5-His-310 that express the correspondent genes with a C-terminal V5 epitope. The spacer and the 310 fragments were PCR-amplified with the respective primers (Table 1) to generate 3' ends of the cDNAs without stop codons and were subsequently subcloned into pEF6/V5-His TOPO (Invitrogen Corp, Carlsbad, Calif.) according to the manufacturer's instructions to obtain cDNAs coding for C-terminal fusion proteins. All generated constructs were confirmed by automated sequencing. Information regarding the primers is available upon request.

GST Fusion protein preparation: XL1-Blue bacteria carrying the pGEX-2T vectors were grown to mid log phase and then induced to express protein by adding 0.25 mM of isopropyl-1-thio-β-D-galactopyranoside (IPTG, Roche Applied Science, Indianapolis, Ind.). The cultures were shaken for 4 h; bacteria were then pelleted and resuspended in NENT buffer (20 mM Tris pH 8, 100 mM NaCl, 1 mM EDTA, 0.5% NP-40). Cell suspensions were sonicated, pelleted and the supernatant collected. The remaining bacteria were then resuspended in NENT buffer plus 2% of N-Lauryl-Sarcosine, pelleted and the supernatants were collected again. The combined supernatants were incubated with Glutathione agarose (Amersham Biosciences, Piscataway, N.J.) overnight at 4° C. The agarose was then pelleted and washed three times in NENT buffer.

Kinase assays: Cell lysates from NIH/3T3 were prepared by resuspending pelleted cells in 500 μl of lysis buffer (50 mMTris, 5 mM EDTA, 250 mM NaCl, 50 mM NaF, 0.1% Triton, 0.1 mM $Na_3VO_4$, plus protease inhibitors). An equal amount of protein for each fraction (100 μg) was immunoprecipitated with a polyclonal anti-cdk2 antibody (De Luca et al., 1997, J Biol Chem, 272, 20971-4). The complexes were pulled down with protein A-Sepharose and washed three times with lysis buffer and twice with lysis buffer containing 400 mM NaCl. The complexes were equilibrated in kinase assay buffer (20 mM HEPES pH 7.4, 10 mM MgAc, 20, 1 mM DTT). In order to detect the in vitro inhibition of cdk2 activity, each sample was incubated with an equal amount (0.1 μg) of each pGEX-2T fusion protein, in a final volume of 20 μl of kinase buffer, using 5 μCi/sample of γ-ATP (Amersham Biosciences, Piscataway, N.J.) and 2 μg of Histone H1 for 30 minutes at 30° C. Kinase assays were repeated at least three times, giving an inter assay standard deviation within 10% after normalization for protein amount. In order to evaluate the in vivo inhibition of cdk2 activity, cdk2 was immuno-precipitated, as described above, from NIH/3T3 cells transiently transfected with 5 μg of pEF6/V5-spacer, pEF6/V5-Spa310 or the vector alone as a control. The immunocomplexes were split in two tubes. A half of each sample was assayed for cdk2 activity in a final volume of 20 μl of kinase buffer with 5 μCi/sample of γ-ATP and 2 μg of Histone H1 for 30 min. at 30° C.; the second one was tested in western blot analysis to confirm that all the samples contained the amount of cdk2 immunoprecipitated. Briefly the samples were separated into 12% SDS polyacrylamide gels (SDS-PAGE), and then transferred into a nitrocellulose membrane (Schleicher & Schuell, Germany). The membrane was blocked with 5% non-fat dry milk in 1×TBST and incubated with the polyclonal anti-cdk2 antibody described above. Anti-rabbit peroxidase conjugated (1:10,000) (Amersham, Ill.) and ECL detection system (Enhanced Chemiluminescence Kit; Du Pont NEN, Boston, Mass.) were used for the detection.

Cdk2 inhibitory activity of the fragments of pRb2/p130 spacer domain: Presented in Table 1 are several constructs containing different portions of the pRb2/p130 spacer region that were prepared, expressed as GST-fusion proteins and assayed for their kinase inhibitory activity. Cdk2 immunocomplexes were precipitated from lysates of exponentially growing NIH/3T3 cells. Each GST fusion protein was added to the immunoprecipitate and the mixture was subjected to a kinase assay using histone H1 as a substrate. Three GST-fusion proteins containing different regions of the spacer domain (Spa, Spb and Spc) were created. We found that an inhibitory effect on histone H1 phosphorylation was exerted only by the first segment (Spa) (see Table 1). Three additional mutants derived from the Spa construct (Spa1, Spa2 and Spa3) were developed and tested. We found that the constructs Spa1, Spa2 and Spa3 proved to have little or no inhibitory effect on the cdk2 activity compared to the immunoprecipitates treated with GST alone and the GST-spacer fusion protein. Therefore, two other constructs (Spa12 and Spa23) overlapping the central part of the Spa region were generated and tested. Since only the GST-fusion protein containing the Spa23 fragment was able to inhibit cdk2 activity, several constructs were finally developed and tested for kinase inhibitory activity by deleting segments of the 5' and 3' ends of the Spa23 (Spa72, Spa92, Spa38, Spa311, Spa310 and Spa312).

FIG. 1 shows the effects on cdk2 activity exhibited by the seven final constructs. The Spa310 construct, spanning the region between the amino acids 641 and 679 (39 amino acids), represented the smallest molecule able to maintain the specific inhibitory ability of the pRb2/p130 spacer domain on cdk2 activity in vitro. The relative kinase activity values shown represent an average of three independent experiments.

TABLE 1

| Construct | | | Segment (from–to) |
|---|---|---|---|
| Spacer | | | 616–828 |
| Spa | | | 616–711 |
| Spb | | | 712–754 |
| Spc | | | 755–828 |
| Spa1 | | | 616–642 |
| Spa2 | | | 641–666 |
| Spa3 | | | 663–711 |
| Spa12 | | | 616–666 |
| Spa23 | | | 641–711 |
| Spa72 | | | 652–711 |
| Spa92 | | | 658–711 |
| Spa38 | | | 641–682 |
| Spa311 | | | 641–702 |
| Spa310 | | | 641–679 |
| Spa312 | | | 641–673 |

| Construct pGEX-2T | Primer 5' | Primer 3' | Nucleotides from to | Base Pair in length | Amino Acids from to | Amino Acids in length | kDa SDS gel | Kinase assay |
|---|---|---|---|---|---|---|---|---|
| Spacer | Sp1 | Sp2 | 1915-2550 | 636 | 616-828 | 212 | 25.4 | P |
| Spa | Sa1 | Sa2 | 1915-2202 | 288 | 616-711 | 96 | 11.5 | P |

TABLE 1-continued

| Construct pGEX-2T | Primer 5' | Primer 3' | Nucleotides from to | Base Pair in length | Amino Acids from to | Amino Acids in length | kDa SDS gel | Kinase assay |
|---|---|---|---|---|---|---|---|---|
| Spb | Sb1 | Sb2 | 2203-2331 | 129 | 712-754 | 43 | 5.2 | N |
| Spc | Sc1 | Sc2 | 2332-2550 | 219 | 755-828 | 73 | 8.8 | N |
| Spa1 | Sa1 | Sa6 | 1915-1995 | 81 | 616-642 | 27 | 3.2 | N |
| Spa2 | Sa3 | Sa4 | 1990-2067 | 78 | 641-666 | 26 | 3.1 | N |
| Spa3 | Sa5 | Sa2 | 2056-2202 | 147 | 663-711 | 49 | 5.8 | N |
| Spa12 | Sa1 | Sa4 | 1915-2067 | 153 | 616-666 | 51 | 6.1 | N |
| Spa23 | Sa3 | Sa2 | 1990-2202 | 213 | 641-711 | 71 | 8.5 | P |
| Spa72 | Sa7 | Sa2 | 2093-2202 | 180 | 652-711 | 60 | 7.3 | N |
| Spa38 | Sa3 | Sa8 | 1990-2175 | 186 | 641-702 | 62 | 7.4 | P |
| Spa311 | Sa3 | Sa11 | 1990-2115 | 126 | 641-682 | 42 | 5.0 | P |
| Spa310 | Sa3 | Sa10 | 1990-2106 | 117 | 641-679 | 39 | 4.7 | P |
| Spa312 | Sa3 | Sa12 | 1990-2088 | 99 | 641-673 | 33 | 3.9 | N |

Nucleotide and amino acid positions, and the fragment length (in base pairs and amino acids) of deletion mutants based on the sequence of the pRb2/p130 spacer domain are shown. The constructs listed in bold, also represented with the black bars, demonstrated a positive inhibitory effect on cdk2 activity. No significant inhibitory effect on cdk2 activity was detected in the other constructs. P=positive, N=negative.

Example 2

Localization of Spacer and Spa310 Molecules in Cells

Expression and localization of Spacer and Spa310 molecules in cells were evaluated as follows:

Immunofluorescence: Exponentially growing NIH/3T3 cells were seeded on two-well micro-chamber slides (Nunc, Naperville, Ill.) and transfected the next day with 1 μg of pEF6/V5-spacer, pEF6/V5-Spa310 or the vector alone (pEF6N5) as a control. Forty-eight hours after transfection, cells were fixed in PBS-buffered 4% paraformaldehyde for 15 min at room temperature and then permeabilized in 0.1% Triton-X 100/PBS before washing and blocking in 0.1% BSA/0.1% Triton-X 100/PBS in 370C for 30 min. The primary antibody used for immunofluorescence was an anti-V5 monoclonal antibody (Invitrogen Corp, Carlsbad, Calif.) that recognizes the epitope present in the constructs. The secondary antibody was a goat anti-mouse conjugated with Alexa-568 (Molecular Probes, Eugene, Oreg.) used at a dilution of 1:2000. DNA was counterstained with DNA fluorochrome 4', 6' diamedino-2-phenylindole (DAPI, Sigma Inc., St. Louis, Mo., USA) and slides were mounted with the SlowFade antifade reagent (Molecular Probes, Eugene, Oreg.). Negative controls were performed with secondary antibodies only. The slides were seen under an inverted Olympus IX70 microscope (Olympus America, Inc. Melville, N.Y.). Fluorescence images were captured with Sensicam QE camera (Cooke Co., Auburn Hills, Mich.) and operated with SlideBook 3.0 software (Intelligent Imaging Innovations Inc., Denver, Colo.) in order to eliminate the background haze and reveal individual foci.

The cells, 48 h after their transfection, were analyzed for immunofluorescence localization of spacer and Spa310 expression, using a monoclonal antibody that specifically recognizes the V5 tag carried by the transfected constructs. Immunofluorescence analysis of transfected cells with anti-V5 antibody revealed a localization of the tagged Spacer and Spa310 proteins in the cytoplasm and in the nucleus, observed as red spots (photograph not presented). Cells were cotinterstained with DNA fluorochrome 4', 6' diamedino-2-phenylindole (DAPI, Simga Inc., St. Louis, Mo., USA) to visualize the nuclei seen as blue spots.

Figure 2:
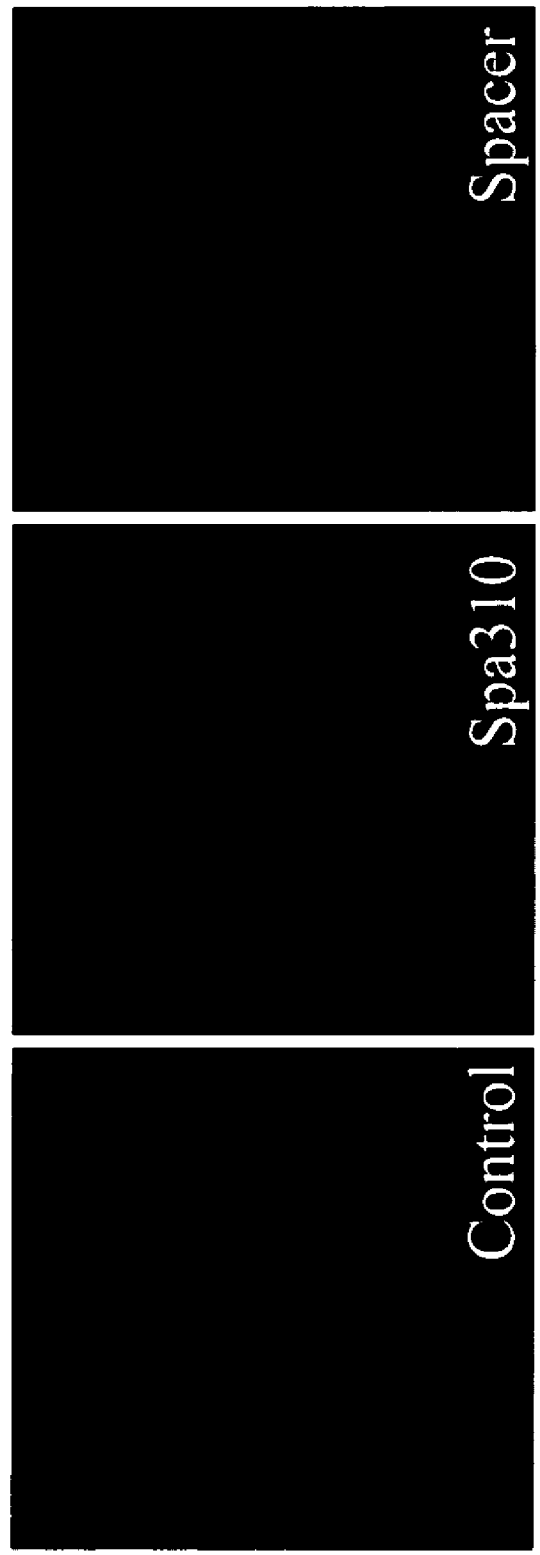
FIG. 2 shows an embodiment of the invention of subcellular localization of the Spacer and Spa310 molecules by immunofluorescent staining.

FIG. 2 shows that the tagged proteins are strongly expressed in the transfected NIH/3T3 cells. The molecules' expression was detected both in the cytoplasm and in the nucleus (red foci) of the transfected cells. The red foci were absent in cells transfected with the control vector, indicating specificity of immunostaining. Similarly, red foci were absent in non-transfected cells. The data shown are representative of three independent experiments.

Example 3

Effect of Spa310 on Endogenous cdk2 Activity

From the above, it can be seen that pRb2/p130 spacer and Spa310 strongly and similarly inhibited cdk2 activity in vitro. In this example, the effect pRb2/p130 spacer and Spa310 on endogenous cdk2 activity is described. The NIH/3T3 cells were transiently transfected with pEF6/V5-spacer, pEF6/V5-Spa310 or the control vector pEF6/V5. At 48 h after transfection, endogenous cdk2 was immunoprecipitated and assayed for kinase activity using histone H1 as a substrate.

Figure 3:
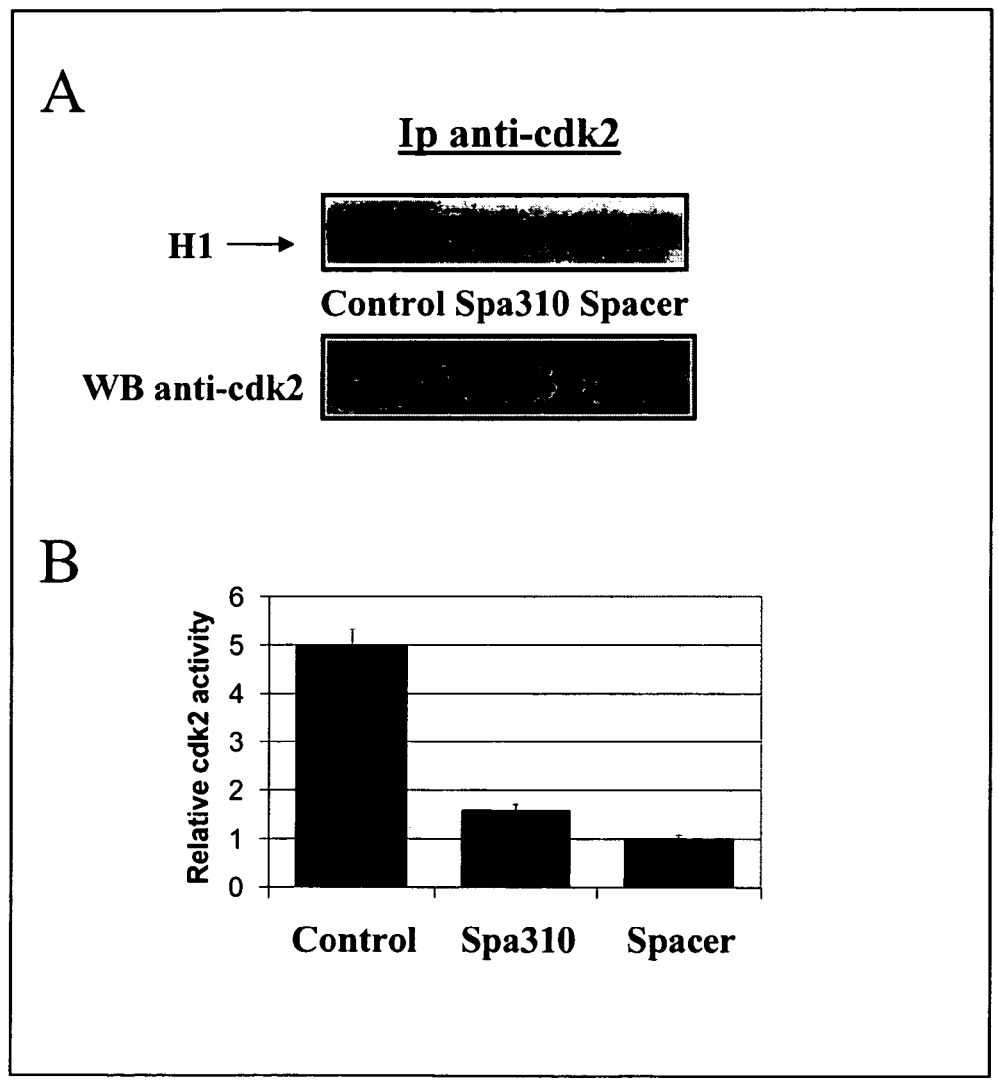
FIGS. 3a and 3b show an embodiment of the invention using SDS-PAGE gels (10%) where Spa310 and the Spacer inhibit endogenous cdk2 activity.

FIGS. 3a and 3b show a significant inhibition of cdk2-dependent histone phosphorylation mediated by both the spacer domain and the Spa310 small peptide expression. In FIG. 3a, asynchronously growing NIH/3T3 cells were transfected with pEF6/V5 vector, pEF6/V5-Spa310 or pEF6/V5-spacer. Forty-eight hours after transfection, cdk2 was immunoprecipitated with anti-cdk2 polyclonal antibody. The immunocomplexes were extensively washed, and split into two tubes. The first half was incubated in kinase assay reaction buffer with 2 μg of histone H1 as a substrate and resolved on 10% gel. Phosphorylation of histone H1 was monitored by autoradiography. The second half was used in western blot analysis to test that the amount of cdk2 immunoprecipitated is the same for all the samples. In FIG. 3b, the relative kinase activity values shown represent an average of three independent experiments.

Example 4

Demonstration of Suppression of Cell Growth by Spa310 Observed by Colony Formation Assay Residues critical for the inhibition of cdk2 activity were identified as described above. The crucial role of cdk2 activity is known to induce the expression of cell cycle-regulatory genes, thus leading to cell cycle progression (Chae et al., 2004, Oncogene, 23, 4084-8; Yu et al., 2004, Biochem Pharmacol, 67, 1907-16). Therefore, inhibiting the phosphorylation ability of this kinase with the Spa310 small molecule should induce cell cycle arrest. In this example, it is shown that these residues are in fact sufficient for cell growth inhibition.

Colony formation assay: The effects of the pRb2/p130 spacer domain and 39 aa small peptide overexpression on cellular growth was examined by colony formation assays. Exponentially growing NIH/3T3 cells were seeded in 100-mm dishes at a density of 5×10⁵ cells per 100 mm dish the day before transfection. Cells were transfected with μg of pEF6/V5-spacer, pEF6/V5-Spa310 or the control vector pEF6/V5 carrying the brasticidin S-resistant gene (bsr) as a selectable marker gene. For selection, blasticidin S hydrochloride (Funakoshi, Tokyo, Japan) was added to the culture medium 48 h after transfection, at a final concentration of 10 μg/mL. After 6 days, 1×10³ of blasticidin S-resistant cells in each well were plated in triplicate in 60-mm dishes, in order to evaluate their colony-forming ability. Cells were then incubated at 37° C. for eight days in a selecting medium containing blasticidin S hydrochloride at a final concentration of 10 μg/mL. Colonies, defined as groups of a minimum of 50 cells, were counted after staining with 2% methylene blue in 95% ethanol.

Figure 4:
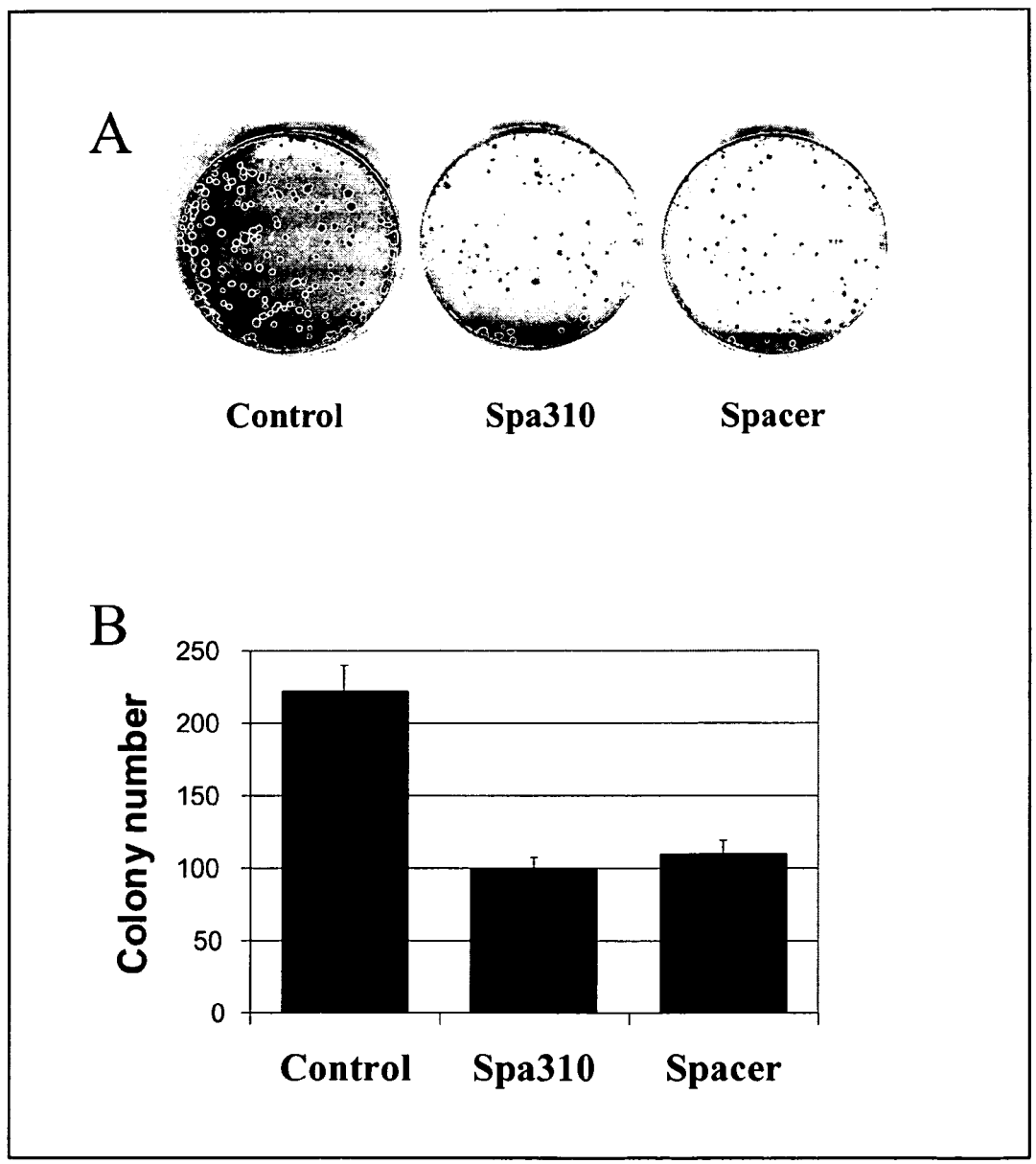
FIGS. 4a and 4b illustrate an embodiment of the invention where Spa310 suppresses colony formation similarly to the full-length spacer domain of pRb2/p130.

As presented in FIGS. 4a and 4b, the spacer region caused a decrease on the ability of the cells to form colonies of about 50% and the Spa310 of about 60%. The control vector alone had no effect on the colonogenic capacity of the cells, demonstrating that the small molecules are, rather than the entire spacer region, indeed sufficient for achieving the growth-inhibited phenotype. In FIG. 4a, NIH/3T3 cells were transfected with pEF6N5 vector, pEF6/V5-Spa310 or pEF6/V5-spacer. Forty-eight hours after transfection, cells were selected with 10 μg/mL of blasticidin S hydrochloride. After six days, an equal number of resistant cells were plated in 60-mm dishes and colony-forming ability was evaluated after eight days of continuous selection. In FIG. 4b, the colony number values shown represent an average of three independent experiments.

Example 5

Effect of Spa310 on Cell Cycle Arrest

To demonstrate that Spa310 small molecule maintains the growth arrest properties, like the full-length Spacer, leading to an arrest in the G0/G1 phase of the cell cycle, cells were transiently transfected with 5 μg of pEF6/V5-spacer, pEF6/V5-Spa310 or the vector alone as a control. A marker plasmid expressing enhanced green fluorescent protein (EGFP)-spectrin was included in the transfection mixture. Control cells, which were not transfected with EGFP-spectrin, were used as the EGFP-negative population. Cells were harvested and examined for their cell cycle states by fluorescence-activated cell sorter (FACS) analysis. After harvest, cells were fixed by adding ice-cold 70% ethanol while vortexing. Fixed cells were stored at 4° C. for at least 30 min and then washed once with PBS. Cells were then stained with 10 μg/ml propidium iodide (Roche Applied Science, Indianapolis, Ind.), 250 μg/ml RNase (Sigma, St. Louis, Mo.) in PBS and incubated at 37° C. for 30 min in the dark. Transfected cells were gated according to their EGFP expression and the DNA content was determined by flow cytometry analysis. The percentage of cells in the different phases of the cell cycle was measured with a FACS Calibur instrument (Becton-Dickinson, San Jose, Calif.) and the data obtained were analyzed by WinMDI 2.8 software.

The inhibition of cdk2 activity caused by the spacer and the Spa310 small molecule had an effect on cell cycle distribution, ultimately leading to cell cycle arrest. Cell cycle analysis/flow cytometry analysis was performed in NIH/3T3 cells transiently transfected with pEF6/V5-spacer, pEF6/V5-Spa310 or the control vector pEF6/V5. A marker plasmid expressing enhanced green fluorescent protein, (EGFP)-spectrin was included in the transfection mixture. At 48 h after transfection, cells were fixed and stained with propidium iodide to determine the DNA content and were simultaneously examined for EGFP expression. Flow cytometry analyses indicated that the spacer and the Spa310 small molecule similarly induced a G0/G1 arrest of the cell cycle, reducing the population of cells in the S phase (FIGS. 5a and 5b).

Figure 5:
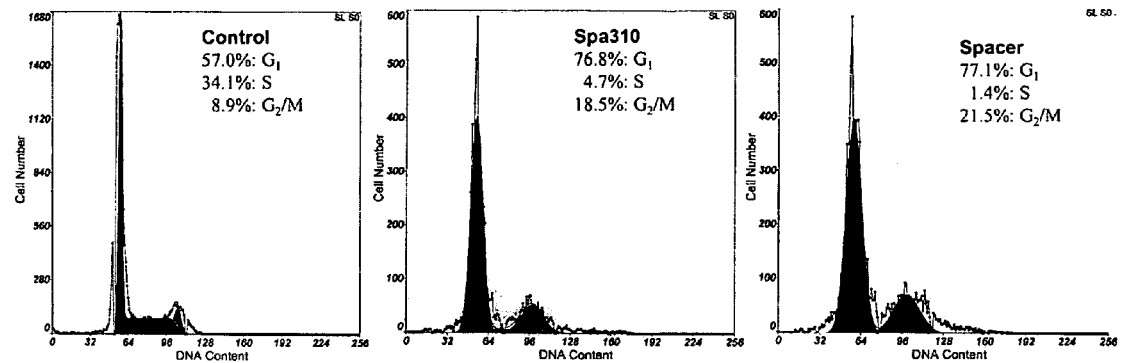
FIGS. 5a and 5b illustrate an embodiment of the invention where the flow cytometry shows the effect of ectopic expression of pRb2/p130-spacer and Spa310 on the cell cycle.
Figure 5:
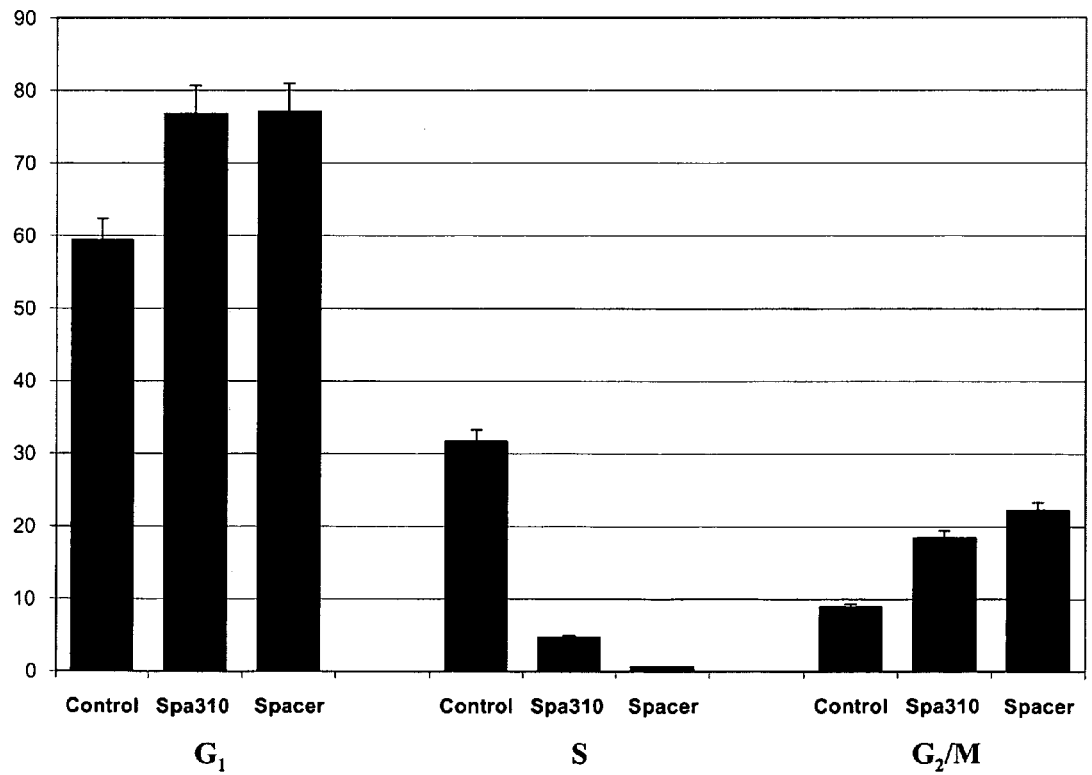

In FIG. 5a, three plasmids were co-expressed with EGFP-spectrin, in a 1:10 ratio, in transient transfection assays. Cells were harvested 48 hours after transfection, stained with propidium iodide and analyzed by flow cytometric gating for both GFP and propidium iodide. Cell cycle distribution was evaluated to determine the distribution of cells through the $G_1$, S and $G_2$/M phases of the cell cycle. In FIG. 5b, the percentages shown represent an average of three independent experiments. Thus, it is shown that the Spa310 small molecule, similarly to the full-length spacer domain of pRb2/p130, acts as a growth suppressor by inducing a $G_0$/$G_1$ arrest of the cell cycle.

Example 6

Treatment of Tumor Growth In Vivo

In this example, it is shown that the Spa310 small molecule does suppress the tumor growth.

Cell Culture: The A549 (wt p53, and wt RB) non-small cell lung cancer cell line was cultured in Ham's F-12 with NaHCO3 (0.75 g NaHCO3/500 ml of Ham's F-12) and 10% (vol/vol) fetal bovine serum (FBS). The cells were cultured at 37° C. in a humidified incubator containing 5% CO2. Cells were harvested, when they reached 70-80% confluence.

Preparation of Tumor Xenografts in Immunodeficient Mice: The animal experiments were carried out in accordance with the Guidelines for the Care and Use of Laboratory Animals (National Institute of Health publication number 85-23) and the institutional guidelines of Temple University. 4-6 week-old female athymic nude mice (CD1, nu/nu) were bought from Charles River Laboratory (Wilmington, Mass.). About a week after the mice arrived, the A549 cells were harvested and then suspended in unsupplemented culture medium without FBS. After the mice were anesthetized by isoflurane inhalation, 4×106 cells in a final volume of 100 μl were injected subcutaneously into the right flank of each mouse by using 1-cc syringes with 25.5-gauge needles.

In Vivo Treatments: The length and width of each tumor were measured every time in triplicates by using a Vernier caliper. Then the median of the measurements was applied to the following formula to calculate the tumor volume: Tumor volume=(the length of the tumor×the width of the tumor)2/2. When the tumors grew up to a volume of about 0.05 cm³, the mice were treated with the peptides. 4 peptides were tested (Spa310, Spa310-Tat, Scramble, and Scramble-Tat). The amino acid sequence of each of the peptides is as follows:

```
                                              (SEQ ID NO:17)
TAT-Spa310: G R K K R R Q R R R P P L T P R R V T
E V R A D T G G L G R S I T S P T T L Y D R Y S S
P P A S T T R (51 amino acids);

(SEQ ID NO:18)
TAT-SCRAMBLE: G R K K R R Q R R R P P T D Y S P A
T R S V G I T R P T L P T S R D S Y T G R E R S V
G P L R T A L T (51 amino acids);

(SEQ ID NO:3)
Spa310: L T P R R V T E V R A D T G G L G R S I T
S P T T L Y D R Y S S P P A S T T R
(39 amino acids); and (SEQ ID NO:19)
SCRAMBLE: T D Y S P A T R S V G I T R P T L P T S
R D S Y T G R E R S V G P L R T A L T
(39 amino acids).
```

For each peptide type, three mice were treated. 50 μl of each peptide type at 1.5 mM in distilled water were injected into the tumoral region every 4 days in the first 5 treatments, and then every 7 days in the last 2 treatments. The tumor sizes were measured before each treatment. Tumor volumes were calculated and plotted on a graph. Tumor suppressive effects of four different peptides (TAT-Spa310, TAT-SCRAMBLE, Spa310 and SCRAMBLE) injected into the mice were as illustrated in FIG. 6.

Thus, it has been demonstrated herein that the small peptide molecules of the present invention are able to inhibit cdk2 activity, inhibit cell cycle progression and induce growth arrest when expressed in cells and promote tumor regression in vivo. The invention, however, should not be limited to the peptides exemplified above. In fact, it may prove to be the case that the most useful pharmacological small molecule peptides and nucleic acids designed and synthesized in light of this disclosure will be second generation derivatives of the exemplified molecules.

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

What is claimed is:

1. A polypeptide comprising a fragment of the full-length pRb2/p130 spacer domain (residues 616-828 of SEQ ID NO:21) or a variant of the fragment, wherein the fragment or the variant is between 34 and 144 amino acids long, wherein the fragment has at least amino acids 641 to 674 of the spacer domain wherein the polypeptide is capable of inhibiting cdk2 kinase activity, wherein the polypeptide is free of fragments containing the contiguous amino acids, 616-711 or 641-711 of the spacer domain.

2. A polypeptide consisting essentially of a fragment of the full-length pRb2/p130 spacer domain or a variant of the fragment, wherein the fragment or the variant is between 34 and 144 amino acids long and is capable of inhibiting cdk2 kinase activity, wherein the fragment has at least amino acids 641 to 674 of the spacer domain and the polypeptide is free of fragments containing the contiguous amino acids 616-711 or 641-711 of the spacer domain.

3. The polypeptide of claim 1 or 2, wherein the fragment is selected from the group consisting of SEQ ID NO:1 (62 amino acids long, designated as Spa38 peptide), SEQ ID NO:2 (42 amino acids long, designated as Spa311 peptide), SEQ ID NO:3 (39 amino acids long, designated as Spa310 peptide), SEQ ID NO:4 (124 amino acids long, designated as Spa319 peptide), SEQ ID NO:5 (131 amino acids long, designated as Spa313 peptide), SEQ ID NO:6 (67 amino acids long, designated as Spa314 peptide), SEQ ID NO:7 (144 amino acids long, designated as Spa315 peptide), SEQ ID NO:8 (87 amino acids long, designated as Spa316 peptide), SEQ ID NO:9 (121 amino acids long, designated as Spa317 peptide), and SEQ ID NO:10 (64 amino acids long, designated as Spa318 peptide).

4. The polypeptide of claim 1 or 2, wherein the polypeptide is a fusion polypeptide.

5. The polypeptide of claim 1 or 2, wherein the polypeptide is conjugated to an agent.

6. A fragment of the full-length spacer domain (residues 616-828 of SEQ ID NO:21) amino acid sequence of pRb2/p130 or a variant thereof, wherein the fragment or the variant is between 34 and 144 amino acids in length and is capable of inhibiting cdk2 kinase activity, wherein the fragment has at least amino acids 641 to 674 of the spacer domain and is free of the contiguous amino acids 616-711 or 641-711 of the spacer domain.

7. The fragment of claim 6, wherein the fragment is selected from the group consisting of SEQ ID NO:1 (62 amino acids long, designated as Spa38 peptide), SEQ ID NO:2 (42 amino acids long, designated as Spa311 peptide), SEQ ID NO:3 (39 amino acids long, designated as Spa310 peptide), SEQ ID NO:4 (124 amino acids long, designated as Spa319 peptide), SEQ ID NO:5 (131 amino acids long, designated as Spa313 peptide), SEQ ID NO:6 (67 amino acids long, designated as Spa314 peptide), SEQ ID NO:7 (144 amino acids long, designated as Spa315 peptide), SEQ ID NO:8 (87 amino acids long, designated as Spa316 peptide), SEQ ID NO:9 (121 amino acids long, designated as Spa317 peptide), and SEQ ID NO: 10 (64 amino acids long, designated as Spa318 peptide).

8. The fragment of claim 3 is fused to a second polypeptide.

9. A composition of any of claims 1, 2 or 6 further comprising a pharmaceutically acceptable carrier.

10. The composition of claim 9, further comprising an anti-cancer agent.

11. The composition of claim 9, wherein the composition is in a sustained release formulation.

* * * * *

SEQUENCE LISTING

<160> NUMBER OF SEQ ID NOS: 21

<210> SEQ ID NO 1
<211> LENGTH: 62
<212> TYPE: PRT
<213> ORGANISM: Homo sapiens

<400> SEQUENCE: 1

Leu Thr Pro Arg Arg Val Thr Glu Val Arg Ala Asp Thr Gly Gly Leu

```
                1               5                  10                 15
Gly Arg Ser Ile Thr Ser Pro Thr Thr Leu Tyr Asp Arg Tyr Ser Ser
                20                 25                 30

Pro Pro Ala Ser Thr Thr Arg Arg Leu Phe Val Glu Asn Asp Ser
        35                 40                 45

Pro Ser Asp Gly Gly Thr Pro Gly Arg Met Pro Pro Gln Pro
        50                 55                 60
```

<210> SEQ ID NO 2
<211> LENGTH: 42
<212> TYPE: PRT
<213> ORGANISM: Homo sapiens

<400> SEQUENCE: 2

```
Leu Thr Pro Arg Arg Val Thr Glu Val Arg Ala Asp Thr Gly Gly Leu
 1               5                  10                 15

Gly Arg Ser Ile Thr Ser Pro Thr Thr Leu Tyr Asp Arg Tyr Ser Ser
                20                 25                 30

Pro Pro Ala Ser Thr Thr Arg Arg Leu
        35                 40
```

<210> SEQ ID NO 3
<211> LENGTH: 39
<212> TYPE: PRT
<213> ORGANISM: Homo sapiens

<400> SEQUENCE: 3

```
Leu Thr Pro Arg Arg Val Thr Glu Val Arg Ala Asp Thr Gly Gly Leu
 1               5                  10                 15

Gly Arg Ser Ile Thr Ser Pro Thr Thr Leu Tyr Asp Arg Tyr Ser Ser
                20                 25                 30

Pro Pro Ala Ser Thr Thr Arg
        35
```

<210> SEQ ID NO 4
<211> LENGTH: 124
<212> TYPE: PRT
<213> ORGANISM: Homo sapiens

<400> SEQUENCE: 4

```
Val Pro Leu Tyr His Phe Tyr Lys Val Ile Glu Val Phe Ile Arg Ala
 1               5                  10                 15

Glu Asp Gly Leu Cys Arg Glu Val Val Lys His Leu Asn Gln Ile Glu
                20                 25                 30

Glu Gln Ile Leu Asp His Leu Ala Trp Lys Pro Glu Ser Pro Leu Trp
        35                 40                 45

Glu Lys Ile Arg Asp Asn Glu Asn Arg Val Pro Thr Cys Glu Glu Val
    50                 55                 60

Met Pro Pro Gln Asn Leu Glu Arg Ala Asp Glu Ile Cys Ile Ala Gly
65                 70                 75                 80

Ser Pro Leu Thr Pro Arg Arg Val Thr Glu Val Arg Ala Asp Thr Gly
                85                 90                 95

Gly Leu Gly Arg Ser Ile Thr Ser Pro Thr Thr Leu Tyr Asp Arg Tyr
                100                105                110

Ser Ser Pro Pro Ala Ser Thr Thr Arg Arg Leu
            115                120
```

<210> SEQ ID NO 5

```
<211> LENGTH: 131
<212> TYPE: PRT
<213> ORGANISM: Homo sapiens

<400> SEQUENCE: 5

Leu Thr Pro Arg Arg Val Thr Glu Val Arg Ala Asp Thr Gly Gly Leu
  1               5                  10                  15

Gly Arg Ser Ile Thr Ser Pro Thr Thr Leu Tyr Asp Arg Tyr Ser Ser
                 20                  25                  30

Pro Pro Ala Ser Thr Thr Arg Arg Leu Phe Val Glu Asn Asp Ser
             35                  40                  45

Pro Ser Asp Gly Gly Thr Pro Gly Arg Met Pro Gln Pro Leu Val
 50                  55                  60

Asn Ala Val Pro Val Gln Asn Val Ser Gly Glu Thr Val Ser Val Thr
 65                  70                  75                  80

Pro Val Pro Gly Gln Thr Leu Val Thr Met Ala Thr Ala Thr Val Thr
                 85                  90                  95

Ala Asn Asn Gly Gln Thr Val Thr Ile Pro Val Gln Gly Ile Ala Asn
                100                 105                 110

Glu Asn Gly Gly Ile Thr Phe Phe Pro Val Gln Val Asn Val Gly Gly
                115                 120                 125

Gln Ala Gln
    130

<210> SEQ ID NO 6
<211> LENGTH: 67
<212> TYPE: PRT
<213> ORGANISM: Homo sapiens

<400> SEQUENCE: 6

Val Pro Thr Cys Glu Glu Val Met Pro Pro Gln Asn Leu Glu Arg Ala
  1               5                  10                  15

Asp Glu Ile Cys Ile Ala Gly Ser Pro Leu Thr Pro Arg Arg Val Thr
                 20                  25                  30

Glu Val Arg Ala Asp Thr Gly Gly Leu Gly Arg Ser Ile Thr Ser Pro
             35                  40                  45

Thr Thr Leu Tyr Asp Arg Tyr Ser Ser Pro Pro Ala Ser Thr Thr Arg
 50                  55                  60

Arg Arg Leu
 65

<210> SEQ ID NO 7
<211> LENGTH: 144
<212> TYPE: PRT
<213> ORGANISM: Homo sapiens

<400> SEQUENCE: 7

Val Pro Leu Tyr His Phe Tyr Lys Val Ile Glu Val Phe Ile Arg Ala
  1               5                  10                  15

Glu Asp Gly Leu Cys Arg Glu Val Val Lys His Leu Asn Gln Ile Glu
                 20                  25                  30

Glu Gln Ile Leu Asp His Leu Ala Trp Lys Pro Glu Ser Pro Leu Trp
             35                  40                  45

Glu Lys Ile Arg Asp Asn Glu Asn Arg Val Pro Thr Cys Glu Glu Val
 50                  55                  60

Met Pro Pro Gln Asn Leu Glu Arg Ala Asp Glu Ile Cys Ile Ala Gly
 65                  70                  75                  80
```

```
Ser Pro Leu Thr Pro Arg Arg Val Thr Glu Val Arg Ala Asp Thr Gly
                85                  90                  95

Gly Leu Gly Arg Ser Ile Thr Ser Pro Thr Thr Leu Tyr Asp Arg Tyr
            100                 105                 110

Ser Ser Pro Pro Ala Ser Thr Thr Arg Arg Leu Phe Val Glu Asn
        115                 120                 125

Asp Ser Pro Ser Asp Gly Gly Thr Pro Gly Arg Met Pro Pro Gln Pro
        130                 135                 140

<210> SEQ ID NO 8
<211> LENGTH: 87
<212> TYPE: PRT
<213> ORGANISM: Homo sapiens

<400> SEQUENCE: 8

Val Pro Thr Cys Glu Glu Val Met Pro Pro Gln Asn Leu Glu Arg Ala
  1               5                  10                  15

Asp Glu Ile Cys Ile Ala Gly Ser Pro Leu Thr Pro Arg Arg Val Thr
             20                  25                  30

Glu Val Arg Ala Asp Thr Gly Gly Leu Gly Arg Ser Ile Thr Ser Pro
         35                  40                  45

Thr Thr Leu Tyr Asp Arg Tyr Ser Ser Pro Pro Ala Ser Thr Thr Arg
     50                  55                  60

Arg Arg Leu Phe Val Glu Asn Asp Ser Pro Ser Asp Gly Gly Thr Pro
 65                  70                  75                  80

Gly Arg Met Pro Pro Gln Pro
             85

<210> SEQ ID NO 9
<211> LENGTH: 121
<212> TYPE: PRT
<213> ORGANISM: Homo sapiens

<400> SEQUENCE: 9

Val Pro Leu Tyr His Phe Tyr Lys Val Ile Glu Val Phe Ile Arg Ala
  1               5                  10                  15

Glu Asp Gly Leu Cys Arg Glu Val Val Lys His Leu Asn Gln Ile Glu
             20                  25                  30

Glu Gln Ile Leu Asp His Leu Ala Trp Lys Pro Glu Ser Pro Leu Trp
         35                  40                  45

Glu Lys Ile Arg Asp Asn Glu Asn Arg Val Pro Thr Cys Glu Glu Val
     50                  55                  60

Met Pro Pro Gln Asn Leu Glu Arg Ala Asp Glu Ile Cys Ile Ala Gly
 65                  70                  75                  80

Ser Pro Leu Thr Pro Arg Arg Val Thr Glu Val Arg Ala Asp Thr Gly
                85                  90                  95

Gly Leu Gly Arg Ser Ile Thr Ser Pro Thr Thr Leu Tyr Asp Arg Tyr
            100                 105                 110

Ser Ser Pro Pro Ala Ser Thr Thr Arg
        115                 120

<210> SEQ ID NO 10
<211> LENGTH: 64
<212> TYPE: PRT
<213> ORGANISM: Homo sapiens

<400> SEQUENCE: 10

Val Pro Thr Cys Glu Glu Val Met Pro Pro Gln Asn Leu Glu Arg Ala
```

```
            1               5                  10                 15
Asp Glu Ile Cys Ile Ala Gly Ser Pro Leu Thr Pro Arg Arg Val Thr
                    20                  25                 30

Glu Val Arg Ala Asp Thr Gly Gly Leu Gly Arg Ser Ile Thr Ser Pro
            35                  40                  45

Thr Thr Leu Tyr Asp Arg Tyr Ser Ser Pro Pro Ala Ser Thr Thr Arg
        50                  55                  60
```

<210> SEQ ID NO 11
<211> LENGTH: 34
<212> TYPE: PRT
<213> ORGANISM: Homo sapiens

<400> SEQUENCE: 11

```
Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
                20                  25                  30

Pro Pro
```

<210> SEQ ID NO 12
<211> LENGTH: 35
<212> TYPE: PRT
<213> ORGANISM: Homo sapiens

<400> SEQUENCE: 12

```
Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
                20                  25                  30

Pro Pro Ala
         35
```

<210> SEQ ID NO 13
<211> LENGTH: 36
<212> TYPE: PRT
<213> ORGANISM: Homo sapiens

<400> SEQUENCE: 13

```
Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
                20                  25                  30

Pro Pro Ala Ser
             35
```

<210> SEQ ID NO 14
<211> LENGTH: 37
<212> TYPE: PRT
<213> ORGANISM: Homo sapiens

<400> SEQUENCE: 14

```
Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
                20                  25                  30

Pro Pro Ala Ser Thr
             35
```

```
<210> SEQ ID NO 15
<211> LENGTH: 38
<212> TYPE: PRT
<213> ORGANISM: Homo sapiens

<400> SEQUENCE: 15

Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
            20                  25                  30

Pro Pro Ala Ser Thr Thr
        35

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Arg Lys Lys Arg Arg Gln Arg Arg Arg
 1               5                  10

<210> SEQ ID NO 17
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Lys Lys Arg Arg Gln Arg Arg Arg Pro Pro Leu Thr Pro Arg
 1               5                  10                  15

Arg Val Thr Glu Val Arg Ala Asp Thr Gly Gly Leu Gly Arg Ser Ile
            20                  25                  30

Thr Ser Pro Thr Thr Leu Tyr Asp Arg Tyr Ser Ser Pro Pro Ala Ser
        35                  40                  45

Thr Thr Arg
    50

<210> SEQ ID NO 18
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Arg Lys Lys Arg Arg Gln Arg Arg Arg Pro Pro Thr Asp Tyr Ser
 1               5                  10                  15

Pro Ala Thr Arg Ser Val Gly Ile Thr Arg Pro Thr Leu Pro Thr Ser
            20                  25                  30

Arg Asp Ser Tyr Thr Gly Arg Glu Arg Ser Val Gly Pro Leu Arg Thr
        35                  40                  45

Ala Leu Thr
    50

<210> SEQ ID NO 19
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Thr Pro Arg Arg Val Thr Glu Val Arg Ala Asp Thr Gly Gly Leu
 1               5                  10                  15

Gly Arg Ser Ile Thr Ser Pro Thr Thr Leu Tyr Asp Arg Tyr Ser Ser
            20                  25                  30

Pro Pro Ala Ser Thr Thr Arg
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Asp Tyr Ser Pro Ala Thr Arg Ser Val Gly Ile Thr Arg Pro Thr
 1               5                  10                  15

Leu Pro Thr Ser Arg Asp Ser Tyr Thr Gly Arg Glu Arg Ser Val Gly
            20                  25                  30

Pro Leu Arg Thr Ala Leu Thr
        35

<210> SEQ ID NO 21
<211> LENGTH: 1139
<212> TYPE: PRT
<213> ORGANISM: Homo sapiens

<400> SEQUENCE: 21

Met Pro Ser Gly Gly Asp Gln Ser Pro Pro Pro Pro Pro Pro
 1               5                  10                  15

Ala Ala Ala Ala Ser Asp Glu Glu Glu Asp Gly Glu Ala Glu
            20                  25                  30

Asp Ala Ala Pro Pro Ala Glu Ser Pro Thr Pro Gln Ile Gln Gln Arg
            35                  40                  45

Phe Asp Glu Leu Cys Ser Arg Leu Asn Met Asp Glu Ala Ala Arg Ala
 50                  55                  60

Glu Ala Trp Asp Ser Tyr Arg Ser Met Ser Glu Ser Tyr Thr Leu Glu
 65                  70                  75                  80

Gly Asn Asp Leu His Trp Leu Ala Cys Ala Leu Tyr Val Ala Cys Arg
                85                  90                  95

Lys Ser Val Pro Thr Val Ser Lys Gly Thr Val Glu Gly Asn Tyr Val
            100                 105                 110

Ser Leu Thr Arg Ile Leu Lys Cys Ser Glu Gln Ser Leu Ile Glu Phe
        115                 120                 125

Phe Asn Lys Met Lys Lys Trp Glu Asp Met Ala Asn Leu Pro Pro His
    130                 135                 140

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
                165                 170                 175

Pro Gln Glu Glu Gln Pro Arg Gln Gln Arg Gly Arg Lys Gln Arg Arg
```

-continued

```
            180                 185                 190
Gln Pro Cys Thr Val Ser Glu Ile Phe His Phe Cys Trp Val Leu Phe
        195                 200                 205
Ile Tyr Ala Lys Gly Asn Phe Pro Met Ile Ser Asp Asp Leu Val Asn
    210                 215                 220
Ser Tyr His Leu Leu Leu Cys Ala Leu Asp Leu Val Tyr Gly Asn Ala
225                 230                 235                 240
Leu Gln Cys Ser Asn Arg Lys Glu Leu Val Asn Pro Asn Phe Lys Gly
                245                 250                 255
Leu Ser Glu Asp Phe His Ala Lys Asp Ser Lys Pro Ser Ser Asp Pro
            260                 265                 270
Pro Cys Ile Ile Glu Lys Leu Cys Ser Leu His Asp Gly Leu Val Leu
        275                 280                 285
Glu Ala Lys Gly Ile Lys Glu His Phe Trp Lys Pro Tyr Ile Arg Lys
    290                 295                 300
Leu Tyr Glu Lys Lys Leu Lys Gly Lys Glu Asn Leu Thr Gly
305                 310                 315                 320
Phe Leu Glu Pro Gly Asn Phe Gly Glu Ser Phe Lys Ala Ile Asn Lys
                325                 330                 335
Ala Tyr Glu Glu Tyr Val Leu Ser Val Gly Asn Leu Asp Glu Arg Ile
            340                 345                 350
Phe Leu Gly Glu Asp Ala Glu Glu Ile Gly Thr Leu Ser Arg Cys
        355                 360                 365
Leu Asn Ala Gly Ser Gly Thr Glu Thr Ala Glu Arg Val Gln Met Lys
    370                 375                 380
Asn Ile Leu Gln Gln His Phe Asp Lys Ser Lys Ala Leu Arg Ile Ser
385                 390                 395                 400
Thr Pro Leu Thr Gly Val Arg Tyr Ile Lys Glu Asn Ser Pro Cys Val
                405                 410                 415
Thr Pro Val Ser Thr Ala Thr His Ser Leu Ser Arg Leu His Thr Met
            420                 425                 430
Leu Thr Gly Leu Arg Asn Ala Pro Ser Glu Lys Leu Glu Gln Ile Leu
        435                 440                 445
Arg Thr Cys Ser Arg Asp Pro Thr Gln Ala Ile Ala Asn Arg Leu Lys
    450                 455                 460
Glu Met Phe Glu Ile Tyr Ser Gln His Phe Gln Pro Asp Glu Asp Phe
465                 470                 475                 480
Ser Asn Cys Ala Lys Glu Ile Ala Ser Lys His Phe Arg Phe Ala Glu
                485                 490                 495
Met Leu Tyr Tyr Lys Val Leu Glu Ser Val Ile Glu Gln Gln Lys
            500                 505                 510
Arg Leu Gly Asp Met Asp Leu Ser Gly Ile Leu Glu Gln Asp Ala Phe
        515                 520                 525
His Arg Ser Leu Leu Ala Cys Cys Leu Glu Val Val Thr Phe Ser Tyr
    530                 535                 540
Lys Pro Pro Gly Asn Phe Pro Phe Ile Thr Glu Ile Phe Asp Val Pro
545                 550                 555                 560
Leu Tyr His Phe Tyr Lys Val Ile Glu Val Phe Ile Arg Ala Glu Asp
                565                 570                 575
Gly Leu Cys Arg Glu Val Val Lys His Leu Asn Gln Ile Glu Glu Gln
            580                 585                 590
Ile Leu Asp His Leu Ala Trp Lys Pro Glu Ser Pro Leu Trp Glu Lys
        595                 600                 605
```

-continued

```
Ile Arg Asp Asn Glu Asn Arg Val Pro Thr Cys Glu Val Met Pro
    610                 615                 620

Pro Gln Asn Leu Glu Arg Ala Asp Glu Ile Cys Ile Ala Gly Ser Pro
625                 630                 635                 640

Leu Thr Pro Arg Arg Val Thr Glu Val Arg Ala Asp Thr Gly Gly Leu
                645                 650                 655

Gly Arg Ser Ile Thr Ser Pro Thr Thr Leu Tyr Asp Arg Tyr Ser Ser
                660                 665                 670

Pro Pro Ala Ser Thr Thr Arg Arg Leu Phe Val Glu Asn Asp Ser
                675                 680                 685

Pro Ser Asp Gly Gly Thr Pro Gly Arg Met Pro Pro Gln Pro Leu Val
690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
                725                 730                 735

Ala Asn Asn Gly Gln Thr Val Thr Ile Pro Val Gln Gly Ile Ala Asn
                740                 745                 750

Glu Asn Gly Gly Ile Thr Phe Phe Pro Val Gln Val Asn Val Gly Gly
                755                 760                 765

Gln Ala Gln Ala Val Thr Gly Ser Ile Gln Pro Leu Ser Ala Gln Ala
770                 775                 780

Leu Ala Gly Ser Leu Ser Ser Gln Val Thr Gly Thr Thr Leu Gln
785                 790                 795                 800

Val Pro Gly Gln Val Ala Ile Gln Ile Ser Pro Gly Gly Gln Gln
                805                 810                 815

Gln Lys Gln Gly Gln Ser Val Thr Ser Ser Asn Arg Pro Arg Lys
                820                 825                 830

Thr Ser Ser Leu Ser Leu Phe Phe Arg Lys Val Tyr His Leu Ala Ala
                835                 840                 845

Val Arg Leu Arg Asp Leu Cys Ala Lys Leu Asp Ile Ser Asp Glu Leu
850                 855                 860

Arg Lys Lys Ile Trp Thr Cys Phe Glu Phe Ser Ile Ile Gln Cys Pro
865                 870                 875                 880

Glu Leu Met Met Asp Arg His Leu Asp Gln Leu Leu Met Cys Ala Ile
                885                 890                 895

Tyr Val Met Ala Lys Val Thr Lys Glu Asp Lys Ser Phe Gln Asn Ile
                900                 905                 910

Met Arg Cys Tyr Arg Thr Gln Pro Gln Ala Arg Ser Gln Val Tyr Arg
                915                 920                 925

Ser Val Leu Ile Lys Gly Lys Arg Lys Arg Arg Asn Ser Gly Ser Ser
                930                 935                 940

Asp Ser Arg Ser His Gln Asn Ser Pro Thr Glu Leu Asn Lys Asp Arg
945                 950                 955                 960

Thr Ser Arg Asp Ser Ser Pro Val Met Arg Ser Ser Ser Thr Leu Pro
                965                 970                 975

Val Pro Gln Pro Ser Ser Ala Pro Pro Thr Pro Thr Arg Leu Thr Gly
                980                 985                 990

Ala Asn Ser Asp Met Glu Glu Glu Glu Arg Gly Asp Leu Ile Gln Phe
                995                 1000                1005

Tyr Asn Asn Ile Tyr Ile Lys Gln Ile Lys Thr Phe Ala Met Lys Tyr
    1010                1015                1020
```

-continued

```
Ser Gln Ala Asn Met Asp Ala Pro Pro Leu Ser Pro Tyr Pro Phe Val
1025                1030                1035                1040

Arg Thr Gly Ser Pro Arg Arg Ile Gln Leu Ser Gln Asn His Pro Val
            1045                1050                1055

Tyr Ile Ser Pro His Lys Asn Glu Thr Met Leu Ser Pro Arg Glu Lys
        1060                1065                1070

Ile Phe Tyr Tyr Phe Ser Asn Ser Pro Ser Lys Arg Leu Arg Glu Ile
    1075                1080                1085

Asn Ser Met Ile Arg Thr Gly Glu Thr Pro Thr Lys Lys Arg Gly Ile
    1090                1095                1100

Leu Leu Glu Asp Gly Ser Glu Ser Pro Ala Lys Arg Ile Cys Pro Glu
1105                1110                1115                1120

Asn His Ser Ala Leu Leu Arg Arg Leu Gln Asp Val Ala Asn Asp Arg
            1125                1130                1135

Gly Ser His
```